(12) United States Patent
Takeo et al.

(10) Patent No.: US 7,194,123 B2
(45) Date of Patent: Mar. 20, 2007

(54) METHOD OF DETECTING ABNORMAL PATTERN CANDIDATES

(75) Inventors: Hideya Takeo, Kaisei-machi (JP); Takashi Imamura, Kaisei-machi (JP)

(73) Assignee: Fuji Photo Film Co., Ltd., Kanagawa-ken (JP)

( * ) Notice: Subject to any disclaimer, the term of this patent is extended or adjusted under 35 U.S.C. 154(b) by 637 days.

(21) Appl. No.: 09/953,909

(22) Filed: Sep. 18, 2001

(65) Prior Publication Data

US 2002/0049376 A1    Apr. 25, 2002

(30) Foreign Application Priority Data

Sep. 18, 2000  (JP)  ............................. 2000-281358
Jul. 12, 2001  (JP)  ............................. 2001-211601

(51) Int. Cl.
*G06K 9/00* (2006.01)

(52) U.S. Cl. ...................... 382/132; 382/128; 128/922; 600/407

(58) Field of Classification Search ................ 382/128, 382/129, 130, 131, 132, 133, 134, 299, 266, 382/269; 128/920, 922; 600/407, 420, 534, 600/425; 250/584, 587, 582; 378/4, 37, 378/62

See application file for complete search history.

(56) References Cited

U.S. PATENT DOCUMENTS

| | | | | |
|---|---|---|---|---|
| 4,537,203 A | * | 8/1985 | Machida | ..................... 600/547 |
| 5,046,147 A | | 9/1991 | Funahashi et al. | ........ 250/327.2 |
| 5,714,764 A | * | 2/1998 | Takeo et al. | ................. 250/587 |
| 5,790,690 A | * | 8/1998 | Doi et al. | ..................... 382/128 |
| 5,850,465 A | * | 12/1998 | Shimura et al. | ............ 382/132 |
| 5,997,478 A | * | 12/1999 | Jackson et al. | ............. 600/437 |
| 6,058,322 A | * | 5/2000 | Nishikawa et al. | ......... 600/408 |
| 6,141,437 A | * | 10/2000 | Xu et al. | ..................... 382/130 |
| 6,185,320 B1 | * | 2/2001 | Bick et al. | .................. 382/132 |

OTHER PUBLICATIONS

Medical Imaging Technology, vol. 12, No. 1, pp. 59, 1994.
Transactions of The Institute of Electronics, Information, and Communication Engineers of Japan, D-II, vol. J75-D-II, No. 3, pp. 663, 1992.
Transactions of The Institute of Electronics, Information, and Communication Engineers of Japan, D-II, vol. J75-DII, No. 7, pp. 1170, 1992.

* cited by examiner

*Primary Examiner*—Jingge Wu
*Assistant Examiner*—Abolfazl Tabatabai
(74) *Attorney, Agent, or Firm*—Sughrue Mion, PLLC

(57) ABSTRACT

Processing for detecting an abnormal pattern candidate embedded in a medical image having been obtained from an image recording operation is performed on an image signal representing the medical image. In cases where the image signal is one which has been subjected to predetermined signal processing, correction processing is performed on the image signal such that the abnormal pattern candidate detecting processing performed on the image signal, which has been subjected to the predetermined signal processing, does not depend upon the predetermined signal processing. The abnormal pattern candidate detecting processing is then performed on the image signal, which has been obtained from the correction processing.

16 Claims, 11 Drawing Sheets

F I G . 4
| $f_7$ | $f_6$ | $f_5$ | $f_4$ | $f_3$ |
|---|---|---|---|---|
| $f_8$ |  |  |  | $f_2$ |
| $f_9$ |  | PIXEL j |  | $f_1$ |
| $f_{10}$ |  |  |  | $f_{16}$ |
| $f_{11}$ | $f_{12}$ | $f_{13}$ | $f_{14}$ | $f_{15}$ |
F I G . 5
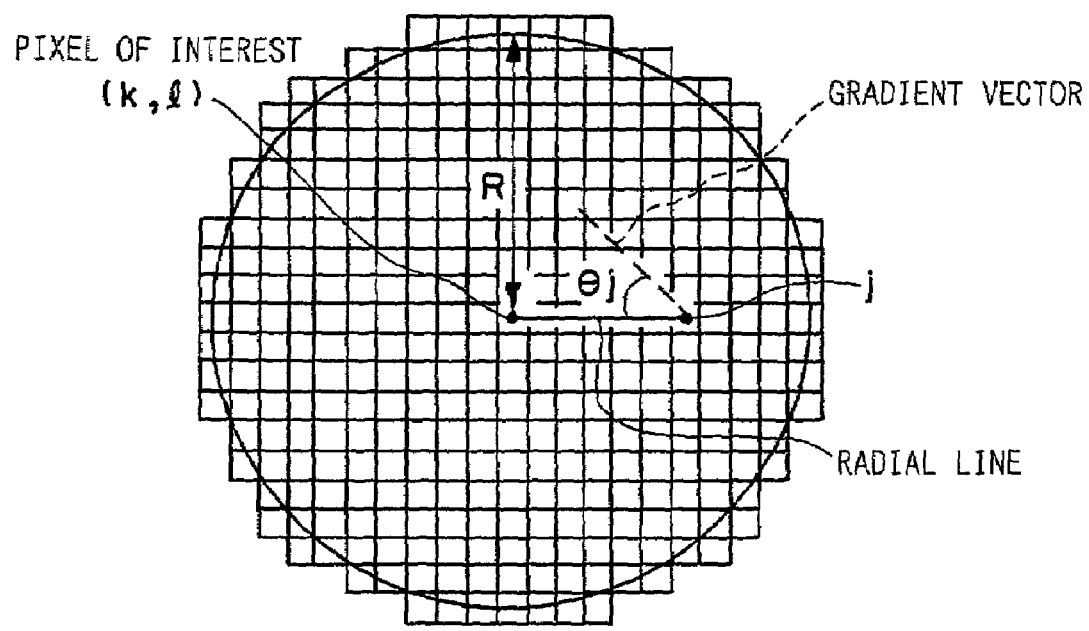

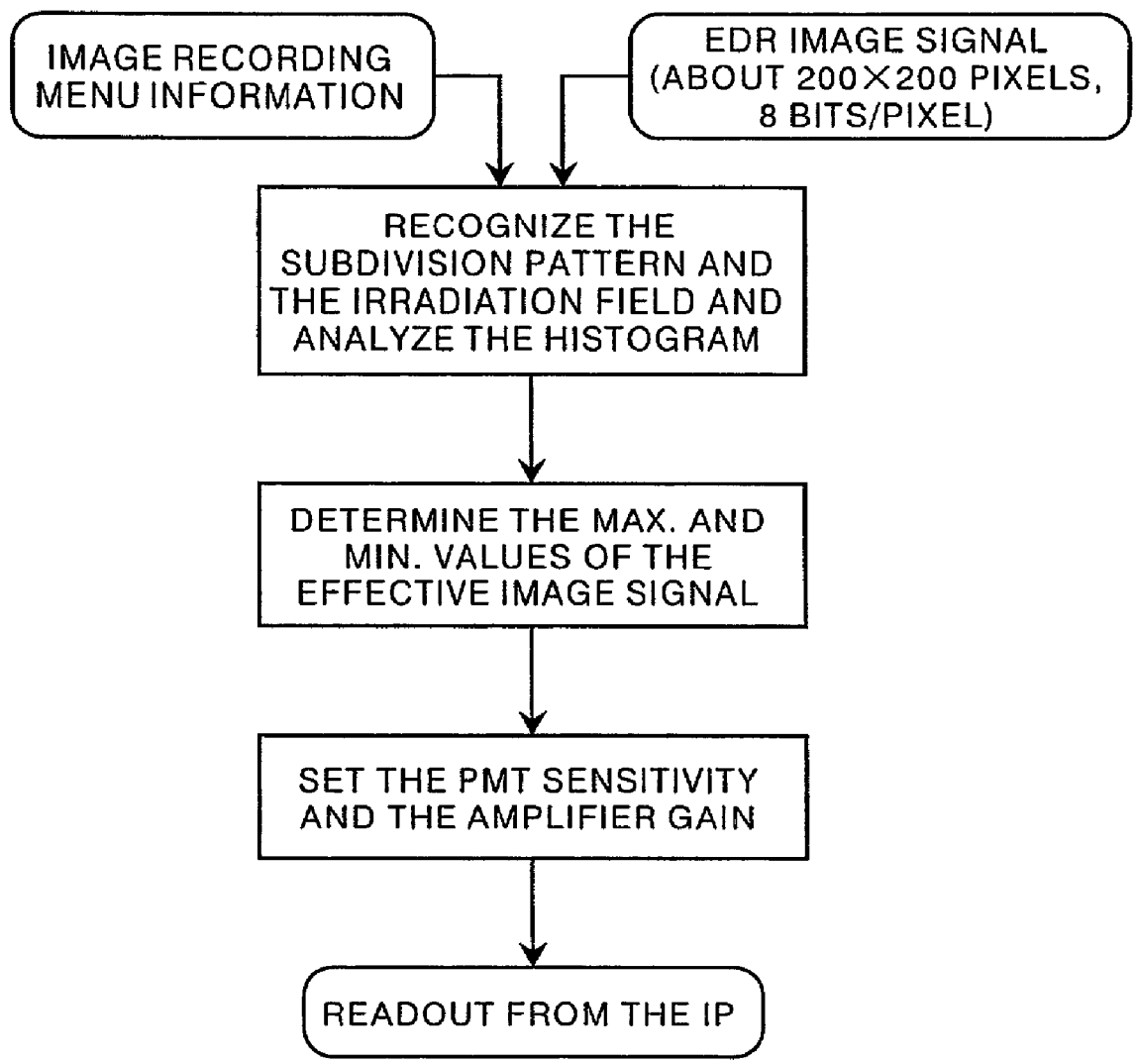

METHOD OF DETECTING ABNORMAL PATTERN CANDIDATES

BACKGROUND OF THE INVENTION

1. Field of the Invention

This invention relates to a method of detecting an abnormal pattern candidate, which is embedded in a medical image. This invention particularly relates to an improvement in a method of detecting an abnormal pattern candidate, wherein processing for detecting the abnormal pattern candidate embedded in a medical image is performed on an image signal, which has been obtained from predetermined signal processing performed in accordance with an imaging environment of the medical image, or the like.

2. Description of the Related Art

In medical fields, radiography for recording radiation images on radiation film and utilizing the recorded radiation images in making diagnosis of an illness has heretofore been used. Recently, in lieu of the conventional radiography, computed radiography (CR) systems have been used widely. The CR systems are also referred to as the digital radiography (DR) systems.

With the CR systems, radiation carrying image information is irradiated to a stimulable phosphor sheet (also referred to as an imaging plate), and a radiation image is thereby recorded on the stimulable phosphor sheet. The stimulable phosphor sheet, on which the radiation image has been stored, is then exposed to stimulating rays, which cause the stimulable phosphor sheet to emit light in proportion to the amount of energy stored thereon during its exposure to radiation. The light emitted by the stimulable phosphor sheet is detected photoelectrically, and an electric signal (an image signal) having thus been obtained is converted into a digital image signal. The digital image signal is then utilized for printing a visible image (a radiation image), which is represented by the image signal, on film with a laser printer or for displaying the visible image on a monitor. The stimulable phosphor sheet employed in the CR systems has the characteristics such that the linearity of the intensity of the emitted light with respect to the radiation dose delivered to the stimulable phosphor sheet is kept over a wide range. Therefore, the CR systems utilizing the stimulable phosphor sheet have the advantages over the techniques for directly recording the radiation image on radiation film in that, for example, a weak fluctuation in image density, or the like, on the image is capable of being detected easily. Also, with the CR systems wherein the digital signals are processed, various kinds of image processings are capable of being performed easily.

Also, particularly for medical diagnoses, techniques referred to as the computer aided diagnosis of medical images (CADM) have been proposed, which aim at more positively utilizing the features of the CR systems.

The techniques for the computer aided diagnosis of medical images, or the like, assist in making diagnoses by reading patterns in an image at the sites of medical treatment. Specifically, in the past, medical specialists visually read patterns in radiation images having been reproduced on recording media, such as X-ray film, display devices, such as cathode ray tube (CRT) display devices, or the like, and made efforts in order to find out abnormal tumor patterns, which represented cancers, or the like, microcalcification patterns, which are smaller than the tumor patterns and have an image density lower than the image density of the tumor patterns, and the like, in the early stages of the diseases. (The tumor patterns, the microcalcification patterns, and the like, will hereinbelow be referred to as the abnormal patterns.) However, in such cases, there is the risk that the abnormal patterns are left unnoticed or are misunderstood due to subjective judgments, depending on differences between the image understanding capabilities of persons, who view the radiation images.

Therefore, the techniques for the computer aided diagnosis of medical images aim at preventing the persons, who view the radiation images, from failing to notice the abnormal patterns and misunderstanding the abnormal patterns, and thereby aim at enabling the persons to make the efficient and accurate diagnosis of an illness. For such purposes, with the techniques for computer aided diagnosis of medical images, an abnormal pattern candidate, which is considered as being an abnormal pattern, is detected. Also, a marking is put on the detected area in order to arouse an attention of the person, who views the radiation image. Alternatively, characteristics of the detected abnormal pattern candidate are indicated quantitatively as materials, which are useful for objective judgments of the person, who views the radiation image. [Reference should be made to "Detection of Tumor Patterns in DR Images (Iris Filter)," Transactions of The Institute of Electronics, Information, and Communication Engineers of Japan, D-II, Vol. J75-D-II, No. 3, pp. 663–670, March 1992; and "Extraction of Microcalcifications Using Morphological Filter with Multiple Structuring Elements," Transactions of The Institute of Electronics, Information, and Communication Engineers of Japan, D-II, Vol. J75-D-II, No. 7, pp. 1170–1176, July 1992.]

As a technique for detecting a tumor pattern candidate, iris filter processing has heretofore been utilized. The iris filter processing utilizes a degree of convergence C of a gradient vector based upon an image density value of a radiation image. Specifically, it has been known that, for example, in a radiation image recorded on negative X-ray film, the image density values of a tumor pattern are slightly smaller than the image density values of the surrounding image areas. The gradient vector at an arbitrary pixel in a tumor pattern is directed to the vicinity of the center point of the tumor pattern. On the other hand, in an elongated pattern, such as a blood vessel pattern, gradient vectors do not converge toward a specific point. Therefore, the distributions of the orientations of the gradient vectors in local area limited regions may be evaluated, and a region, in which the gradient vectors converge toward a specific point, may be detected. The thus detected region maybe taken as a tumor pattern candidate, which is considered as being a tumor pattern. The iris filter processing is based on such fundamental concept. Steps of algorithms of the iris filter processing will be described hereinbelow.

(Step 1) Calculation of Gradient Vectors

For each pixel j among all of the pixels constituting a given image, the orientation θ of the gradient vector of the image signal representing the image is calculated with Formula (3) shown below.

$$\theta = \tan^{-1} \frac{(f_3 + f_4 + f_5 + f_6 + f_7) - (f_{11} + f_{12} + f_{13} + f_{14} + f_{15})}{(f_1 + f_2 + f_3 + f_{15} + f_{16}) - (f_7 + f_8 + f_9 + f_{10} + f_{11})} \quad (3)$$

As illustrated in FIG. 4, $f_1$ through $f_{16}$ in Formula (3) represent the pixel values (i.e., the image signal values) corresponding to the pixels located at the peripheral areas of a mask, which has a size of five pixels (located along the column direction of the pixel array)×five pixels (located along the row direction of the pixel array) and which has its center at the pixel j.

(Step 2) Calculation of the Degree of Convergence of Gradient Vectors

Thereafter, for each pixel among all of the pixels constituting the given image, the pixel is taken as a pixel of interest, and the degree of convergence C of the gradient vectors with respect to the pixel of interest is calculated with Formula (4) shown below.

$$C = (1/N) \sum_{j=1}^{N} \theta_j \quad (4)$$

As illustrated in FIG. 5, in Formula (4) shown above, N represents the number of the pixels located in the region inside of a circle, which has its center at the pixel of interest and has a radius R, and $\theta j$ represents the angle made between the straight line, which connects the pixel of interest and each pixel j located in the circle, and the gradient vector at the pixel j, which gradient vector has been calculated with Formula (3) shown above. Therefore, in cases where the orientations of the gradient vectors of the respective pixels j converge toward the pixel of interest, the degree of convergence C represented by Formula (4) shown above takes a large value.

The gradient vector of each pixel j, which is located in the vicinity of a tumor pattern, is directed approximately to the center area of the tumor pattern regardless of the level of the contrast of the tumor pattern. Therefore, it can be regarded that the pixel of interest associated with the degree of convergence C, which takes a large value, is the pixel located at the center area of the tumor pattern. On the other hand, in a linear pattern, such as a blood vessel pattern, the orientations of the gradient vectors are biased to a certain orientation, and therefore the value of the degree of convergence C is small. Accordingly, a tumor pattern is capable of being detected by taking each of all pixels, which constitute the image, as the pixel of interest, calculating the value of the degree of convergence C with respect to the pixel of interest, and rating whether the value of the degree of convergence C is or is not larger than a predetermined threshold value. Specifically, the iris filter has the features over an ordinary difference filter in that the iris filter is not apt to be adversely affected by blood vessel patterns, mammary gland patterns, or the like, and can efficiently detect tumor patterns.

In actual processing, such that the detection performance unaffected by the sizes and shapes of tumor patterns may be achieved, it is contrived to adaptively change the size and the shape of the filter. FIG. 6 shows an example of the filter. The filter illustrated in FIG. 6 is different from the filter shown in FIG. 5. With the filter of FIG. 6, the degree of convergence is rated only with the pixels, which are located along radial lines extending radially from a pixel of interest in 32 directions at 11.25 degree intervals.

Also, for each of the directions of the radial lines, the output value obtained for the pixels ranging from the center point (i.e., the pixel of interest) to a pixel, which is located along the radial line and at which the maximum degree of convergence is obtained, is taken as the degree of convergence with respect to the direction of the radial line. The mean value of the values of the degree of convergence, which have been obtained for all of the 32 directions, is then calculated. The mean value of the values of the degree of convergence having thus been calculated is taken as the degree of convergence C with respect to the pixel of interest. Specifically, the degree of convergence $Ci(n)$, which is obtained for the pixels ranging from the pixel of interest to the n-th pixel located along the i-th radial line, is calculated with Formula (5) shown below.

$$Ci(n) = \frac{1}{n - R\min + 1} \sum_{1=R\min}^{n} \cos\theta_{i1}, \quad R\min \leq n \leq R\max \quad (5)$$

wherein Rmin and Rmax respectively represent the minimum value and the maximum value having been set for the radius of the tumor pattern, which is to be detected.

Specifically, with Formula (5), the degree of convergence $Ci(n)$ is calculated with respect to all of the pixels, which are located along each of the radial lines and fall within the range from a starting point to an end point, the starting point being set at the pixel of interest, the end point being set at one of pixels that are located between a position at the length of distance corresponding to the minimum value Rmin having been set for the radius of the tumor pattern, which is to be detected, and a position at the length of distance corresponding to the maximum value Rmax.

Thereafter, the degree of convergence C of the gradient vectors is calculated with Formulas (6) and (7) shown below.

$$Ci_{\max} = \max_{R\min \leq n \leq R\max} Ci(n) \quad (6)$$

$$C = (1/32) \sum_{i=1}^{32} Ci_{\max} \quad (7)$$

Formula (6) shown above represents the maximum value of the degree of convergence $Ci(n)$ obtained for each of the radial lines with Formula (5). Therefore, the region from the pixel of interest to the pixel associated with the degree of convergence $Ci(n)$, which takes the maximum value, may be considered as being the region of the tumor pattern candidate. By the detection of such regions for all of the radial lines with Formula (6), it is possible to judge the shape of the peripheral edge of the region, which may be regarded as the tumor pattern candidate.

With Formula (6), the maximum values of the degree of convergence within the aforesaid regions are calculated for all directions of the radial lines. Thereafter, with Formula (7), the mean value of the maximum values of the degree of convergence within the aforesaid regions, which maximum values have been given by Formula (6) for all directions of the radial lines, is calculated. The calculated mean value is compared with a predetermined threshold value T. From the results of the comparison, a judgment is made as to whether there is or is not a probability that the region having its center at the pixel of interest will be the abnormal pattern candidate.

The region, in which the degree of convergence C with Formula (7) is rated, is similar to the iris of the human's eye, which expands or contracts in accordance with the brightness of the external field. The size and the shape of the region is changed adaptively in accordance with the distribution of the gradient vectors. Therefore, the filter used is referred to as the iris filter.

The calculation of the degree of convergence Ci(n) may be performed by using Formula (5') shown below in lieu of Formula (5).

$$Ci(n) = \frac{1}{n - R\min + 1} \sum_{l=R\min}^{n} \cos \theta_{il}, R\min \leq n \leq R\max \quad (5')$$

Specifically, with Formula (5'), the degree of convergence Ci(n) is calculated with respect to all of the pixels, which are located along each of the radial lines and fall within the range from a starting point to an end point, the starting point being set at a pixel that is located at the length of distance corresponding to the minimum value Rmin having been set for the radius of the tumor pattern to be detected, which length of distance is taken from the pixel of interest, the end point being set at one of pixels that are located between the position at the length of distance corresponding to the minimum value Rmin and the position at the length of distance corresponding to the maximum value Rmax, which length of distance is taken from the pixel of interest.

(Step 3) Rating of the Shape and Form of the Tumor Pattern Candidate

In general, patterns of malignant tumors have the characteristics of the shapes and forms described below.

1) The side edges are irregular.

2) The shape is close to an ellipse.

3) The region inside of the pattern has a convex or concave image density distribution.

Therefore, a judgment is made as to the shape and form by considering these characteristics such that patterns of normal tissues may be eliminated from the detected pattern candidate, and such that only the tumor pattern candidate, which is considered as being a tumor pattern, can be detected. The characteristic measures used in making the judgment include the spreadness, the elongation, the roughness of side edges, the circularity, and the degree of convexity or concavity (i.e., the entropy) of the image density distribution in the region inside of the pattern. The characteristic measures may be compared with a predetermined threshold value, and a final judgment may be made as to whether the detected pattern is or is not a tumor pattern candidate.

By carrying out the steps described above, the iris filter is capable of efficiently detecting a tumor pattern.

How morphological operation processing is performed will be described hereinbelow. The morphological operation processing is the technique for detecting a microcalcification pattern, which is one of the characteristic forms of mammary cancers as in the cases of the tumor patterns. The morphological operation processing is performed by using a multiscale $\lambda$ and a structure element (i.e., a mask) B. The morphological processing has the features in that, for example, (1) it is efficient for extracting a calcification pattern itself, (2) it is not affected by complicated background information, and (3) the extracted calcification pattern does not become distorted. Specifically, the morphological operation processing is advantageous over ordinary differentiation processing in that it can more accurately detect the geometrical information concerning the size, the shape, and the density distribution of the calcification pattern. The morphological operation processing is performed in the manner described below.

(Fundamental Morphological Operation)

In general, the morphological operation is expanded as the theory of sets in an N-dimensional space. As an aid in facilitating the intuitive understanding, the morphological operation will be described hereinbelow with reference to a two-dimensional gray level image.

The gray level image is considered as a space, in which a point having coordinates (x, y) has a height corresponding to an image density value f(x, y). In this case, it is assumed that the image signal representing the image density value f(x, y) is a high luminance—high signal level type of image signal, in which a low image density (i.e., a high luminance when the image is displayed on a CRT display device) is represented by a high image signal level.

Firstly, as an aid in facilitating the explanation, a one-dimensional function f(x) corresponding to the cross-section of the two-dimensional gray level image is considered. It is assumed that structure element g used in the morphological operation is a symmetric function of Formula (8) which is symmetric with respect to the origin.

$$g^s(x) = g(-x) \quad (8)$$

It is also assumed that the value is 0 in a domain of definition G, which is represented by Formula (9).

$$G = \{-m, -m+1, \ldots, -1, 0, 1, \ldots, m\} \quad (9)$$

In such cases, the fundamental forms of the morphological operation are very simple operations performed with Formulas (10), (11), (12), and (13) shown below.

$$\text{dilation:} [fG^S](i) = \max\{f(i-m), \ldots, f(i), \ldots, f(i+m)\} \quad (10)$$

$$\text{erosion:} [fG^S](i) = \min\{f(i-m), \ldots, f(i), \ldots, f(i+m)\} \quad (11)$$

$$\text{opening:} f_g = (fg^S)g \quad (12)$$

$$\text{closing:} f^g = (fg^S)g \quad (13)$$

Specifically, as illustrated in FIG. 7A, the dilation processing is the processing for retrieving the maximum value in a width of ±m (the value determined in accordance with a structure element B) having its center at a pixel of interest. As illustrated in FIG. 7B, the erosion processing is the processing for retrieving the minimum value in the width of ±m having its center at the pixel of interest. The opening processing is equivalent to the searching of the maximum value after the searching of the minimum value. Also, the closing processing is equivalent to the searching of the minimum value after the searching of the maximum value. More specifically, as illustrated in FIG. 7C, the opening processing is equivalent to the processing for smoothing the image density curve f(x) from the low luminance side, and removing a convex image density fluctuating area (i.e., the area at which the luminance is higher than that of the surrounding areas), which fluctuates in a range spatially narrower than the mask size of 2 m. Also, as illustrated in FIG. 7D, the closing processing is equivalent to the processing for smoothing the image density curve f(x) from the high luminance side, and removing a concave image density fluctuating area (i.e., the area at which the luminance is lower than that of the surrounding areas), which fluctuates in the range spatially narrower than the mask size of 2 m.

In cases where the image signal representing the image density value f(x) is a high image density—high signal level type of image signal, in which a high image density is represented by a high image signal level, the relationship between the image density value f(x) and the image signal value becomes reverse to the relationship between the image density value f(x) and the image signal value in the high luminance—high image signal level type of image signal. Therefore, the dilation processing, which is performed on the high image density—high signal level type of image signal, coincides with the erosion processing, which is performed on the high luminance—high signal level type of image signal as shown in FIG. 7B. The erosion processing, which is performed on the high image density—high signal level type of image signal, coincides with the dilation processing, which is performed on the high luminance—high signal level type of image signal as shown in FIG. 7A. The opening processing, which is performed on the high image density—high signal level type of image signal, coincides with the closing processing, which is performed on the high luminance—high signal level type of image signal as shown in FIG. 7D. Also, the closing processing, which is performed on the high image density—high signal level type of image signal, coincides with the opening processing, which is performed on the high luminance—high signal level type of image signal as shown in FIG. 7C.

The morphological operation processing is herein described with respect to the high luminance—high signal level type of image signal (i.e, the image signal representing the luminance value).

(Application to Detection of Calcification Patterns)

In order for a calcification pattern to be detected, it is considered to employ a difference method, in which a smoothed image signal is subtracted from the original image signal. However, with a simple smoothing method, it is difficult to discriminate the calcification pattern from an elongated non-calcification pattern (for example, a pattern of the mammary gland, a blood vessel, mammary gland supporting tissues, or the like). Therefore, Kobatake of Tokyo University of Agriculture and Technology, et al. have proposed amorphological filter, which is represented by Formula (14) shown below and is based upon the opening operation using a multi-structure element. [Reference should be made to "Extraction of Microcalcifications Using Morphological Filter with Multiple Structuring Elements," Transactions of The Institute of Electronics, Information, and Communication Engineers of Japan, D-II, Vol. J75-D-II, No. 7, pp. 1170–1176, July 1992; and "Fundamentals of Morphology and Its Application to Mammogram Processing," Medical Imaging Technology, Vol. 12, No. 1, January 1994.]

$$P = f - \min_{i \in (1,...,M)} \{(f \ominus B_i) \oplus B_i\} \quad (14)$$
$$= f - \min_{i \in (1,...,M)} \{f_{Bi}\}$$

In Formula (14), Bi (wherein i=1, 2, ..., M) represents, for example, four linear structure elements B (in this case, M=4) shown in FIG. 8. (The four structure elements, as a whole, will hereinbelow be referred to as the multi-structure element.) In cases where the structure element B is set to be larger than the calcification pattern to be detected, a calcification pattern, which is a convex signal change area finer than the structure element B (i.e., which is an image area fluctuating in a spatially narrow range), is removed in the opening processing. On the other hand, an elongated non-calcification pattern is longer than the structure element B. Therefore, in cases where the inclination of the non-calcification pattern (i.e, the direction along which the non-calcification pattern extends) coincides with one of the directions of the four structure elements Bi, the non-calcification pattern remains unremoved after the opening processing, i.e. the operation of the second term of Formula (14), has been performed. Therefore, when the smoothed image signal obtained from the opening processing (i.e. the signal representing the image, from which the calcification pattern has been removed) is subtracted from the original image signal f, an image can be obtained which contains only the microcalcification pattern candidate. This is the concept behind Formula (14).

As described above, in cases where the image signal is of the high image density—high signal level type, the image density value of the calcification pattern is smaller than the image density values of the surrounding image areas, and the calcification pattern constitutes a concave signal change area with respect to the surrounding areas. Therefore, the closing processing is applied in lieu of the opening processing, and Formula (15) shown below is applied in lieu of Formula (14).

$$P = f - \min_{i \in (1,...,M)} \{(f \oplus B_i) \ominus B_i\} \quad (15)$$
$$= f - \min_{i \in (1,...,M)} \{f_{Bi}\}$$

However, it often occurs that a non-calcification pattern having the same size as the size of the calcification pattern remains in the obtained image. In such cases, the signal, which represents the non-calcification pattern and is contained in P of Formula (14), is removed by utilizing the differentiation information based upon the morphological operation performed with Formula (16) shown below.

$$M_{grad} = (1/2) \times \{f \lambda B - f \lambda B\} \quad (16)$$

A large value of Mgrad indicates a high possibility of being a calcification pattern. Therefore, a calcification pattern candidate Cs is capable of being detected with Formula (17) shown below.

IF $P(i, j) \geq T1$ and $M_{grad}(i,j) \geq T2$

Then $C_S(i, j) = P$ else $C_S(i,j) = 0$ (17)

In Formula (17), T1 and T2 represent the predetermined threshold values, which are capable of being determined experimentally.

However, a non-calcification pattern, which has a size different from the size of the calcification pattern, can be removed by only the comparison of P of Formula (14) and the predetermined threshold value T1. Therefore, in cases where there is no risk that a non-calcification pattern having the same size as the size of the calcification pattern remains, it is sufficient for the condition of the first term of Formula (17), i.e. the condition of $P(i, j) \geq T1$, to be satisfied.

Finally, the cluster Cc of the calcification pattern is detected by the combination of the opening operation and the closing operation of the multi-scale in accordance with Formula (18) shown below.

$$C_C = C_S \lambda_1 B - \lambda_3 B \lambda_2 B \quad (18)$$

In Formula (18), $\lambda_1$ and $\lambda_2$ are respectively determined by the maximum distance of the calcification pattern to be combined and the maximum radius of the isolated pattern to be removed, and $\lambda_3 = \lambda_1 + \lambda_2$.

As for the high luminance—high signal level type of image signal, the morphological filter is operated in the manner described above. In cases where the image signal is of the high image density—high signal level type (in which a pixel of a high image density has a large digital signal value), the relationship between the opening operation and the closing operation is reversed.

In the CR systems described above, a read-out sensitivity and contrast adjusting function, which is referred to as the exposure data recognizer (EDR), is employed. With the EDR, a preliminary read-out operation (hereinbelow referred to as the "preliminary readout") is performed in order to approximately ascertain the image information of a radiation image, which has been stored on a stimulable phosphor sheet. Also, an image signal, which is to be used in reproducing a visible image capable of being used for diagnostic purposes, or the like, is obtained from a final read-out operation (hereinbelow referred to as the "final readout"). During the preliminary readout, the stimulable phosphor sheet is coarsely scanned with stimulating rays, which have an energy level lower than the energy level of the stimulating rays used in the final readout. In accordance with the image information having been obtained from the preliminary readout, read-out conditions for the final read-out, such as a read-out sensitivity (hereinbelow often referred to as the S value) and a latitude (hereinbelow often referred to as the L value), are adjusted such that the visible image reproduced from the image signal, which is obtained from the final readout, can have good image quality, e.g. an appropriate image density and an appropriate contrast, and can serve as an effective tool in, particularly, the efficient and accurate diagnosis of an illness. The read-out sensitivity and contrast adjusting function is a processing for eliminating a difference in imaging environment, containing image recording conditions under which the radiation image is recorded, photoelectric reading conditions, and the like, and enabling the visible image having an appropriate image density and an appropriate contrast to be reproduced. Ordinarily, the read-out sensitivity and contrast adjusting function is referred to as the normalization processing. Besides the CR systems, the normalization processing, such as the EDR, is also capable of being performed on medical images, which are obtained with medical image forming apparatuses, such as computed tomography (CT) scanners and magnetic resonance imaging (MRI) apparatuses.

With the EDR described above, the read-out conditions are optimized in accordance with the image information having been obtained from the preliminary readout, and thereafter the final readout is performed under the optimized read-out conditions. Such that time loss due to the preliminary readout is eliminated, and the processing and the apparatus are kept simple, an EDR, wherein the preliminary readout need not be performed, has also been proposed in, for example, U.S. Pat. No. 5,046,147.

With the proposed signal processing technique, the detection range is set to be sufficiently wide (for example, approximately 4 orders of ten) with respect to an assumed intensity of the light emitted by a stimulable phosphor sheet, and the entire radiation image is thereby read out to obtain an image signal. From the obtained image signal, an appropriate read-out sensitivity and an appropriate latitude are determined. Thereafter, in accordance with the determined read-out sensitivity and the determined latitude, the obtained image signal is transformed into an image signal, which is equivalent to the image signal, which would be obtained if the image were again read out under the conditions of the determined read-out sensitivity and the determined latitude.

With the proposed signal processing technique, the setting of the photoelectric read-out means with respect to the intensity of the stimulating rays irradiated to the stimulable phosphor sheet, the setting of the sensitivity, the setting of the dynamic range, and the like, need not be performed again, and an image signal necessary to reproduce an appropriate image is capable of being obtained with the calculation processing alone. Therefore, recently, the proposed signal processing technique (EDR) is popular.

FIG. 9 is a flow chart showing the EDR processing. How the EDR processing, which is one of the techniques for the normalization processing, is performed will be described hereinbelow.

As illustrated in FIG. 9, an EDR image signal (a preliminary read-out image signal) is obtained from the preliminary readout, which is performed before the final readout and in which a stimulable phosphor sheet (hereinbelow often referred to as the imaging plate, i.e. IP) is coarsely scanned with a weak laser beam. Also, image recording menu information is inputted when an ID information for identifying the patient is registered. From the image signal and the image recording menu information, a subdivision pattern, in which the recording area on the stimulable phosphor sheet is divided into a plurality of subdivisions, is determined. Also, an irradiation field in each of the subdivisions is recognized. Thereafter, a histogram of the image signal (the image density), which corresponds to the region inside of the recognized irradiation field, is formed. FIGS. 10A and 10B are graphs showing examples of histograms of image signals corresponding to regions inside of irradiation fields. As illustrated in FIGS. 10A and 10B, the histograms of the image signals have patterns inherent to the image recording menus. The image recording menu is determined by the portion of the object, the image of which is recorded, and the image recording method, such as simple image recording or contrasted image recording. By the utilization of such characteristics of the histogram, the maximum value $S_1$ and the minimum value $S_2$ of the effective image signal can be detected. In this manner, the read-out conditions for the final readout are capable of being adjusted such that the image density and the contrast may become appropriate.

The read-out conditions are specified by the two parameters, i.e., the read-out sensitivity (S value) and the latitude (L value) described above. Specifically, the read-out conditions determine the sensitivity of a photomultiplier and the gain of a multiplier. The final read-out image signal, which is obtained by performing the final readout under the adjusted read-out conditions, has been normalized to predetermined digital values regardless of the kind of the object and the environment under which the image of the object is recorded. Therefore, regardless of the imaging environment (containing the read-out environment), the image processing, which is performed on the final read-out image signal, and the storage of the final read-out image signal are capable of being performed easily. Further, from the final read-out image signal, a visible image having an appropriate image density or luminance and an appropriate contrast is capable of being reproduced on photographic film, a CRT monitor, or the like.

FIG. 11 is a graph showing a principle, upon which the EDR processing is based.

With reference to FIG. 11, a first quadrant shows the relationship between the dose of X-rays irradiated to an IP and the intensity of light emitted by the IP. The intensity of the light emitted by the IP is in direct proportion to the dose of X-rays irradiated to the IP over a wide range of the dose. The relationship is one of the features of the IP which are worthy of special mention.

The second quadrant shows the EDR function, i.e., shows the relationship between the intensity of the emitted light, which is entered into read-out means, and an output digital signal, which is obtained under the read-out conditions having been adjusted by the EDR.

The third quadrant shows how the image enhancement processing (i.e., processing in the frequency domain and gradation processing) is performed for obtaining display characteristics appropriate for diagnostic purposes, or the like. In FIG. 11, an example of a gradation processing curve appropriate for a mamma image is shown.

The fourth quadrant shows a characteristic curve of an output photograph in the CR system. Specifically, the dose of X-rays irradiated to the IP is plotted on the horizontal axis, and the density on photographic film is plotted on the vertical axis extending downwardly. The characteristic curve takes on the form of an inverted characteristic curve of an X-ray photograph obtained with an ordinary fluorescent intensifying screen-film system. As described above, with the EDR, the maximum value $S_1$ and the minimum value $S_2$ of the image signal effective for diagnostic purposes, or the like, are detected from the histogram of the EDR image signal. Also, the read-out conditions are adjusted such that the maximum value $S_1$ and the minimum value $S_2$ may be transformed respectively into values $Q_1$ and $Q_2$, which have been set previously for each image recording menu.

Specifically, as for an example (i), in which the dose of X-rays irradiated to the IP is high and the image signal width is narrow, the EDR adjusts the read-out conditions as indicated by (A). As for an example (ii), in which the dose of X-rays irradiated to the IP is low and the image signal width is wide, the EDR adjusts the read-out conditions as indicated by (B). As a result, the characteristic curve of the CR system varies for different doses of X-rays and different image signal widths, and an appropriate image density and an appropriate contrast are capable of being obtained in every case. This feature is markedly different from the characteristic curve of the conventional fluorescent intensifying screen-film system.

As described above, in the CR, the read-out conditions are defined by the two parameters, i.e., the read-out sensitivity and the latitude. FIG. 12 is a graph showing the relationship between the intensity of light emitted by an IP and an output value, the graph serving as an aid in explaining a read-out sensitivity (S value) and a latitude (L value), which serve as read-out conditions. The S value is the index representing the read-out sensitivity, and the L value is the index representing the latitude. The read-out conditions, under which the image signal is obtained, are capable of being known from the two indexes.

The S value, which is the index representing the read-out sensitivity, is defined by Formulas (19) and (20) shown below.

$$S = 4 \times 10^{4-Sk} \tag{19}$$

$$Sk = \log(X/20(mR)) + 3.0 \tag{20}$$

wherein Sk is the value representing the intensity of light emitted by the IP, which intensity of light corresponds to the median value (511 in the cases of 10 bits) of the digital pixel values.

The value Sk representing the intensity of light emitted by the IP is of the logarithmic scale, wherein the intensity of emitted light, which is obtained from the IP having been exposed to a dose of 20 mR (=5.16×10$^{-6}$C/kg) at a tube voltage of 25 kVp of an Mo tube, is taken as a reference value of 3.0. In cases where the Sk value is equal to the reference value of 3.0, the S value is equal to 40. As the dose of X-rays irradiated to the IP becomes relatively large, the Sk value becomes large and the S value becomes small. This means that, since the intensity of light emitted by the IP is large, even if the read-out sensitivity is low, a sufficient signal can be taken up.

The L value is the index representing the range of the intensity of light emitted by the IP, which range has its center at the Sk value and is digitized. The L value is defined by Formula (21) shown below.

$$L = (1024/1) \times \{(\log S_1 - \log S_2)/(Q_1 - Q_2)\} \tag{21}$$

wherein $S_1$ and $S_2$ represent the aforesaid characteristic values detected by the EDR, and $Q_1$ and $Q_2$ represent the pixel values corresponding respectively to the characteristic values $S_1$ and $S_2$.

For example, in cases where images having the same contrast of energy from X-rays are respectively read out with an L value of 1 and an L value of 2, the digital values obtained with the L value of 1 have a difference two times as large as the difference of the digital values obtained with the L value of 2.

Specifically, ordinarily, the EDR processing described above may be represented by Formula (1) shown below.

$$Qout = (RQ/Rq)(Qin - qm)/L + Qm$$

$$\text{where } L = (\Delta q/Rq)/(\Delta Q/RQ) \tag{1}$$

wherein Qin represents the original image signal, Qout represents the image signal after being subjected to the EDR processing, Δq represents the width (latitude) of the original image signal, ΔQ represents the width (predetermined value) of the image signal after being subjected to the EDR processing, qm represents the reference value of the image signal before being subjected to the EDR processing, Qm represents the signal value which the reference value qm takes after the EDR processing has been performed, Rq represents the range of the image signal Qin, and RQ represents the range of the image signal Qout.

With the EDR, the read-out conditions (i.e., the S value and the L value) are adjusted by primarily aiming at obtaining a reproduced visible image, in which the range effective as the medical image (i.e, the range other than the background region corresponding to the region on the stimulable phosphor sheet, upon which region the radiation impinged directly without passing through the object) has an appropriate image density and an appropriate contrast, such that the reproduced visible image can serve as an effective tool in, particularly, the efficient and accurate diagnosis of an illness. For example, as for an image originally having a narrow dynamic range, the signal width is set to be wide, and the contrast of the image is positively enhanced, such that a visible image having good image quality can be reproduced and used as an effective tool in, particularly, the accurately and efficient diagnosis of an illness.

As described above, with the normalization processing, the image density and the contrast of the entire image are always set to be predetermined levels regardless of the imaging environment. However, the image density and the contrast of an abnormal pattern, which is embedded in the image, do not necessarily become predetermined levels. Therefore, in cases where abnormal pattern candidate detecting processing is performed on the image signal, which has been subjected to the normalization processing, the level of detection of the abnormal pattern candidate depends upon the imaging environment. In such cases, a result is brought about, which is contrary to the aim of the computer aided medical image diagnosing system for keeping the capability of detection of the abnormal pattern candidate at a predetermined level.

Specifically, in the iris filter processing described above, the threshold value T, which is utilized in making a judgment as to whether a pattern is or is not a tumor pattern candidate, is a predetermined value having been experimentally set previously. (The threshold value T is the threshold value compared with the iris filter output value C represented by Formula (7) shown above. In cases where C≧T, it is judged that the pattern is a tumor pattern candidate. In cases where C<T, it is judged that the pattern is not a tumor pattern candidate.) Also, in the morphological operation processing described above, the threshold values T1 and T2, which are utilized in making a judgment as to whether a pattern is or is not an abnormal pattern candidate, are the predetermined values having been experimentally set previously. However, as described above, the image signal, on which the abnormal pattern candidate detecting processing is performed, has the signal values having been obtained by adjusting the read-out sensitivity and the latitude with the normalization processing. Also, the signal values contain radiation quantum noise contained in the radiation image. The levels of the image signal components associated with the components of quantum noise also fluctuate in accordance with the adjustment of the read-out sensitivity and the latitude made with the normalization processing.

In the manner described above, the levels of the image signal components associated with the components of quantum noise also fluctuate due to the normalization processing. In such cases, if the threshold value, which is utilized in making a judgment as to whether a pattern is or is not an abnormal pattern candidate, is always set at a predetermined value, there will be the risk that the image signal components associated with quantum noise will be detected by mistake as the image signal components representing the abnormal pattern candidate. Specifically, as a result of the normalization processing performed on the image signal in order to eliminate the effects of the imaging environment, the abnormal pattern candidate detecting processing is affected by the imaging environment.

Besides the normalization processing performed on the image signal obtained with the CR systems, as for an image signal obtained with the image forming apparatuses, such as the CT scanners, in cases where the image signal is one which has been subjected to predetermined signal processing as in the cases of the normalization processing, there is the risk that the same problems as those described above will occur.

SUMMARY OF THE INVENTION

The primary object of the present invention is to provide a method of detecting an abnormal pattern candidate, wherein processing for detecting the abnormal pattern candidate is performed on an image signal, which has been subjected to predetermined signal processing in accordance with an imaging environment of a medical image, or the like, and wherein a level of detection of the abnormal pattern candidate is capable of being kept at a predetermined level instead of depending upon the signal processing.

A first method of detecting an abnormal pattern candidate in accordance with the present invention is characterized by performing correction processing on an image signal such that abnormal pattern candidate detecting processing performed on the image signal does not depend upon predetermined signal processing, such as normalization processing, the correction processing preventing levels of image signal components associated with radiation quantum noise from becoming high or low in accordance with predetermined signal processing, a level of erroneous detection of quantum noise and a level of detection of an abnormal pattern candidate being always kept approximately at predetermined levels, the level of detection of the abnormal pattern candidate being thereby kept at a predetermined level.

Specifically, the present invention provides a first method of detecting an abnormal pattern candidate, in which processing for detecting an abnormal pattern candidate embedded in a medical image having been obtained from an image recording operation is performed on an image signal representing the medical image, the method comprising the steps of:

i) in cases where the image signal is an image signal which has been subjected to predetermined signal processing, performing correction processing on the image signal such that the abnormal pattern candidate detecting processing performed on the image signal, which has been subjected to the predetermined signal processing, does not depend upon the predetermined signal processing, and ii) performing the abnormal pattern candidate detecting processing on the image signal, which has been obtained from the correction processing.

In the first method of detecting an abnormal pattern candidate in accordance with the present invention, the abnormal pattern candidate detecting processing should preferably be a processing, in which iris filter processing is performed on the image signal, and a tumor pattern candidate is thereby detected as the abnormal pattern candidate. Alternatively, the abnormal pattern candidate detecting processing should preferably be a processing, in which morphological operation processing is performed on the image signal, and a microcalcification pattern candidate is thereby detected as the abnormal pattern candidate.

Also, in the first method of detecting an abnormal pattern candidate in accordance with the present invention, the predetermined signal processing should preferably be signal processing performed in accordance with an index value, which represents an imaging environment of the medical image. For example, in cases where the signal processing is normalization processing, which may be represented by Formula (1) shown below, the correction processing should preferably be a processing, which may be represented by Formula (2) shown below. In such cases, the signal processing, which has been transformed into the signal processing (the normalization processing, or the like) with respect to a reference imaging environment, is capable of being performed.

$$Q\text{out}=(RQ/Rq)(Q\text{in}-qm)/L+Qm \qquad (1)$$

$$Q\text{out}'=(L/L0)(Q\text{out}-Qm)+Qm \qquad (2)$$

wherein $Q\text{in}$ represents the image signal before being subjected to the signal processing, $Q\text{out}$ represents the image signal after being subjected to the signal processing, qm represents the predetermined signal value before being subjected to the signal processing, Qm represents the value which qm takes after the signal processing has been performed, L=(Δq/Rq)/(ΔQ/RQ), Δq represents the width (latitude) of the image signal before being subjected to the signal processing, ΔQ represents the width (predetermined value) of the image signal after being subjected to the signal processing, Rq represents the signal range of Qin, RQ represents the signal range of Qout, L0 represents the reference L value, and Qout' represents the image signal after being subjected to the correction processing.

In such cases, the first method of detecting an abnormal pattern candidate in accordance with the present invention may be modified such that a lower limit value of L is determined previously, and the value of L is set at the lower limit value of L in cases where the value of L in Formula (2) is at most equal to the lower limit value having been determined. Also, the first method of detecting an abnormal pattern candidate in accordance with the present invention may be modified such that an upper limit value of L is determined previously, and the value of L is set at the upper limit value of L in cases where the value of L in Formula (2) is at least equal to the upper limit value having been determined.

Further, the first method of detecting an abnormal pattern candidate in accordance with the present invention should preferably be modified such that a threshold value, which is utilized in the abnormal pattern candidate detecting processing in making a judgment as to whether a pattern is or is not the abnormal pattern candidate, is corrected in accordance with the index value, which represents the imaging environment of the medical image.

A second method of detecting an abnormal pattern candidate in accordance with the present invention is characterized by correcting a threshold value, which is utilized for threshold value processing in abnormal pattern candidate detecting processing, such that the threshold value is converted into a threshold value in predetermined signal processing, which acts as reference signal processing, detection of an abnormal pattern candidate being capable of being performed under detecting conditions identical with those in the signal processing acting as reference signal processing, a level of detection of the abnormal pattern candidate being thereby kept at a predetermined level.

Specifically, the present invention also provides a second method of detecting an abnormal pattern candidate, in which processing for detecting an abnormal pattern candidate embedded in a medical image having been obtained from an image recording operation is performed on an image signal representing the medical image, the method comprising the step of:

in cases where the image signal is an image signal which has been subjected to predetermined signal processing, correcting a threshold value, which is utilized in the abnormal pattern candidate detecting processing in making a judgment as to whether a pattern is or is not the abnormal pattern candidate, in accordance with predetermined signal processing, which acts as reference signal processing for the medical image.

In the second method of detecting an abnormal pattern candidate in accordance with the present invention, as in the first method of detecting an abnormal pattern candidate in accordance with the present invention, the abnormal pattern candidate detecting processing should preferably be a processing, in which iris filter processing is performed on the image signal, and a tumor pattern candidate is thereby detected as the abnormal pattern candidate. Alternatively, the abnormal pattern candidate detecting processing should preferably be a processing, in which morphological operation processing is performed on the image signal, and a microcalcification pattern candidate is thereby detected as the abnormal pattern candidate.

Also, in the second method of detecting an abnormal pattern candidate in accordance with the present invention, the predetermined signal processing should preferably be signal processing performed in accordance with an index value, which represents an imaging environment of the medical image.

Further, in the second method of detecting an abnormal pattern candidate in accordance with the present invention, the index value, which represents the imaging environment acting as a reference imaging environment, should preferably be a width (reference latitude L0) of the image signal under the imaging environment acting as the reference imaging environment.

With the first method of detecting an abnormal pattern candidate in accordance with the present invention, the correction processing is performed on the image signal, which has been subjected to the predetermined signal processing, such as the normalization processing, such that the abnormal pattern candidate detecting processing performed on the image signal does not depend upon the predetermined signal processing. Therefore, the levels of image signal components associated with radiation quantum noise in the medical image do not become high or low in accordance with the predetermined signal processing, which is performed in accordance with the imaging environment of the medical image, or the like, or the levels of the image signal components associated with radiation quantum noise are converted into levels under the reference signal processing, such as the signal processing performed under the reference imaging environment. As a result, the level of erroneous detection of quantum noise and the level of detection of the abnormal pattern candidate are always kept approximately at predetermined levels. Accordingly, the level of detection of the abnormal pattern candidate is capable of being kept at a predetermined level.

With the first method of detecting an abnormal pattern candidate in accordance with the present invention, the lower limit value of L may be determined previously, and the value of L may be set at the lower limit value of L in cases where the value of L in Formula (2) is at most equal to the lower limit value having been determined. In such cases, even if L takes a particularly abnormal value, the correction is capable of being made appropriately.

Also, with the first method of detecting an abnormal pattern candidate in accordance with the present invention, the upper limit value of L maybe determined previously, and the value of L may be set at the upper limit value of L in cases where the value of L in Formula (2) is at least equal to the upper limit value having been determined. In such cases, even if L takes a particularly abnormal value, the correction is capable of being made appropriately.

With the second method of detecting an abnormal pattern candidate in accordance with the present invention, the threshold value, which is utilized for the threshold value processing in the abnormal pattern candidate detecting processing, is corrected in accordance with the reference signal processing, which corresponds to the reference imaging environment, or the like. In this manner, the threshold value, which is utilized for the threshold value processing in the abnormal pattern candidate detecting processing, is corrected into the threshold value, which has been converted for the predetermined signal processing corresponding to the reference imaging environment, or the like. Therefore, the level of detection of the abnormal pattern candidate is capable of being kept at the detection level under the reference signal processing (the reference imaging environment, or the like).

BRIEF DESCRIPTION OF THE DRAWINGS

FIG. 4 is an explanatory view showing a mask for calculating gradient vectors, FIG. 5 is an explanatory view showing the concept behind the degree of convergence of a gradient vector with respect to a pixel of interest, FIG. 9 is a flow chart showing EDR processing.

DESCRIPTION OF THE PREFERRED EMBODIMENTS

The present invention will hereinbelow be described in further detail with reference to the accompanying drawings.

Figure 1A:
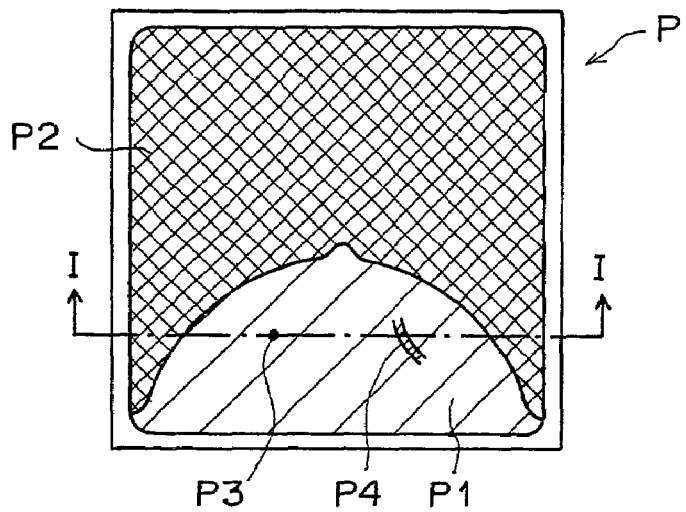
FIG. 1A is an explanatory view showing an X-ray image P containing an image P1 of the mamma, which acts as an object.
Figure 1B:
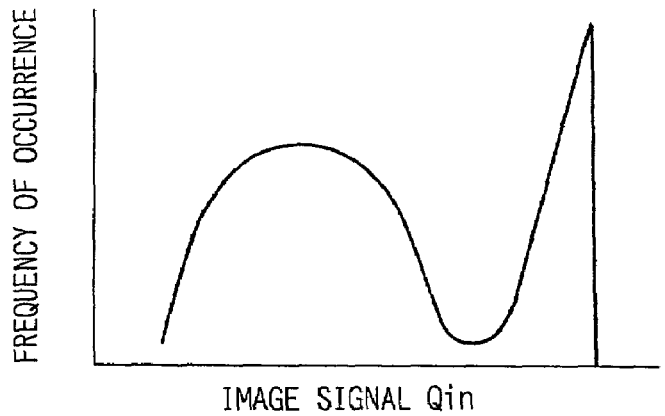
FIG. 1B is a graph showing a histogram of a digital image signal, which has been obtained by reading out the X-ray image P of FIG. 1A in accordance with a predetermined S value and a predetermined L value, which have been determined with EDR processing.
Figure 1C:
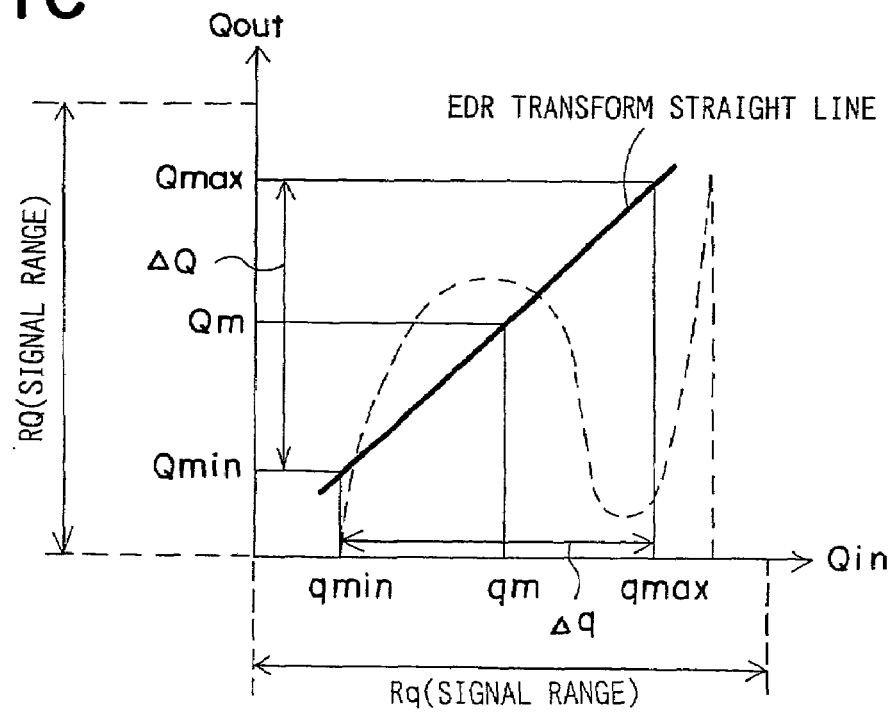
FIG. 1C is a graph showing a function for transform processing, which is performed on an image signal Qin and with the EDR processing.

FIG. 1A is an explanatory view showing an X-ray image P containing an image P1 of the mamma, which acts as an object. FIG. 1B is a graph showing a histogram of a digital image signal Qin, which has been obtained by reading out the X-ray image P of FIG. 1A in accordance with a predetermined read-out sensitivity S and a predetermined latitude $\Delta q$, which have been determined with EDR processing. FIG. 1C is a graph showing how an input-output transform is performed on the image signal Qin and with the EDR processing (input: Qin, output: Qout).

The image signal before being subjected to the EDR processing may be represented by Qin. The image signal after being subjected to the EDR processing may be represented by Qout. The signal width (the latitude) of the entire image signal before being subjected to the EDR processing, which signal width is detected by analyzing the histogram, may be represented by qmin–qmax. The value (a predetermined value), which has been set so as to be taken by qmin after the EDR processing has been performed, maybe represented by Qmin. The value (a predetermined value), which has been set so as to be taken by qmax after the EDR processing has been performed, may be represented by Qmax. A reference value (e.g., a median value) of the input image signal Qin may be represented by qm. Also, the value (a predetermined value), which has been set so as to be taken by the reference value qm after the EDR processing has been performed, may be represented by Qm (e.g., 511 in the cases of 10 bits). In such cases, the EDR transform illustrated in FIG. 1C may be represented by Formula (0;a) shown below.

$$Q\text{out}=(\Delta Q/\Delta q)\times(Q\text{in}-qm)+Qm \qquad (0;a)$$

where $\Delta q=qmax-qmin$, and $\Delta Q=Qmax-Qmin$.

The L value is the signal width before the EDR processing is performed, which signal width corresponds to the unit signal width after the EDR processing has been performed. Therefore, in cases where the signal range of the image signal Qin is represented by Rq (e.g., Rq=256 in the cases of 8 bits), and the signal range of the image signal Qout is represented by RQ (e.g., RQ=1024 in the cases of 10 bits), the L value may be represented by the formula shown below.

$$L=(\Delta q/Rq)/(\Delta Q/RQ)$$

In cases where Formula (0;a) shown above is represented by use of the L value, Formula (1) shown below is obtained.

$$Q\text{out}=(RQ/Rq)(Q\text{in}-qm)/L+Qm \qquad (1)$$

Formula (1) shown above represents the image signal Qout, which has been obtained by performing the EDR transform processing on the image signal Qin. In Formula (1), (RQ/Rq) means compensation for the number of bits of the signal before the EDR processing is performed and after the EDR processing has been performed.

Figure 2:
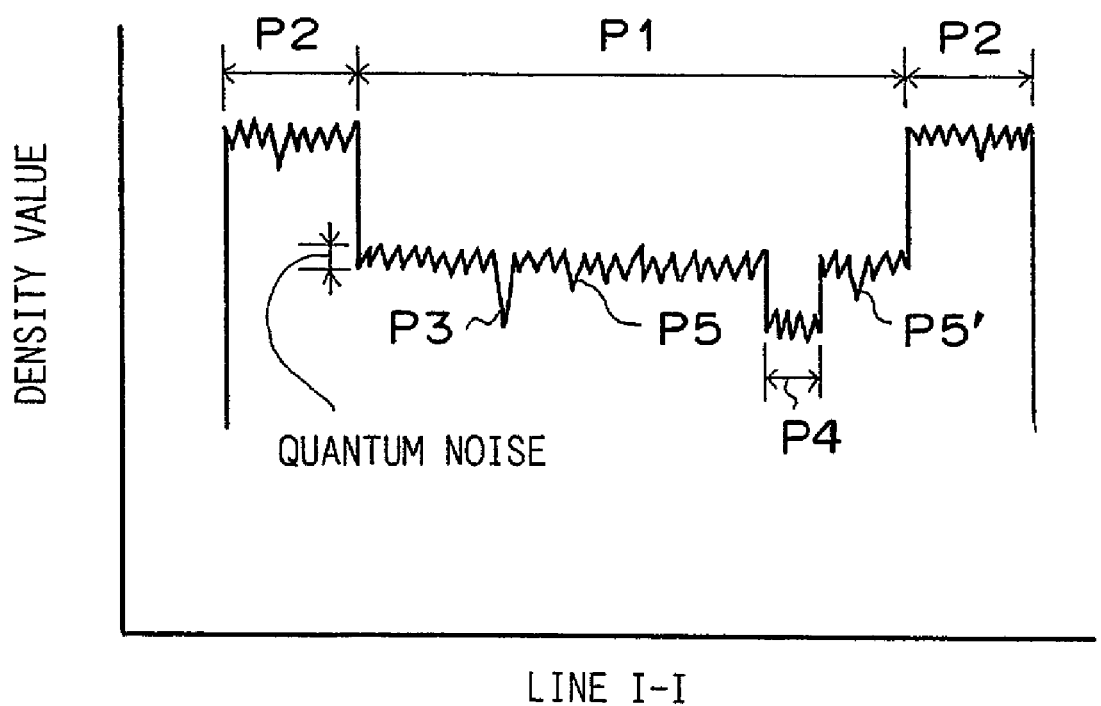
FIG. 2 is a graph showing a distribution of image density values (the digital image signal) representing the X-ray image P, the distribution being taken along line I—I of FIG. 1A.

FIG. 2 is a graph showing a distribution of image density values (the digital image signal) representing the X-ray image P, the distribution being taken along line I—I of FIG. 1A.

In the X-ray image P, the region other than the mamma image P1 is a background region P2, upon which the X-rays impinged directly without passing through the mamma acting as the object during an operation for recording the X-ray image P. The background region P2 has the highest image density in the X-ray image P. In this embodiment, the image signal (the image density value) is the high image density—high digital value type of image signal, which has a high digital image value for a high image density of the X-ray image P.

On the line I—I of FIG. 1A, a microcalcification pattern P3, which represents a characteristic pattern of cancer, and a blood vessel pattern P4, which extends in a predetermined direction, are located. Further, as illustrated in FIG. 2, quantum noise P of the X-rays is contained in the entire image.

The operation processing with the morphological filter represented by Formula (14) shown above is performed on the image signal. In the operation processing with the morphological filter, structure elements, which are smaller than the blood vessel pattern P4 and larger than the microcalcification pattern P3, are used. By the operation processing with the morphological filter, the blood vessel pattern P4 is removed, and only the microcalcification pattern P3 is detected.

However, by the operation processing with the morphological filter, an area P5' of the noise component P5, or the like, which has the same size as the size of the microcalcification pattern P3, is detected together with the microcalcification pattern P3. Therefore, the area P5' of the noise component, or the like, is removed by utilizing the differentiation information based upon the morphological operation performed with Formula (16).

A large value of Mgrad of Formula (16) represents a high possibility that the pattern will be the microcalcification pattern P3. Therefore, a calcification pattern candidate Cs is capable of being detected by making the calculation with Formula (17) shown above. In Formula (17), the threshold values T1 and T2 take the predetermined values. However, since the image signal Qout is one which has been subjected to the EDR processing described above, the image signal Qout depends upon the signal width (latitude) $\Delta q$, which is the index value representing the imaging environment of the original image signal Qin. Therefore, the level of the noise component P5 fluctuates in accordance with the signal width $\Delta q$, which is the index value representing the imaging environment of the original image signal Qin. Accordingly, the noise components, which are capable of being removed with Formula (17), vary for different imaging environments. As a result, the level of detection of the abnormal pattern candidate fluctuates.

Figure 3:
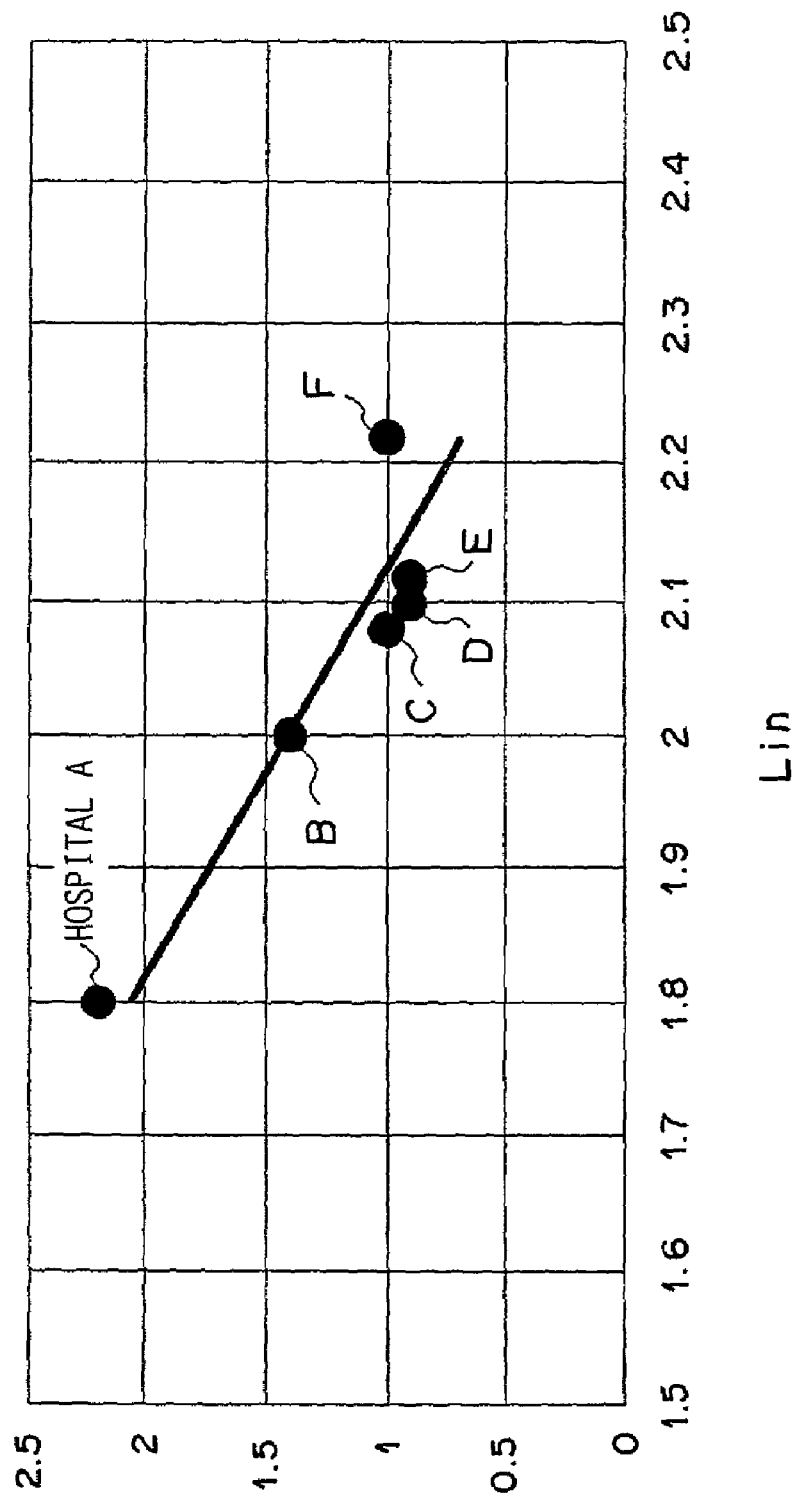
FIG. 3 is a graph showing numbers of abnormal pattern candidates, which have been detected in hospitals under different imaging environments.
Figure 6:
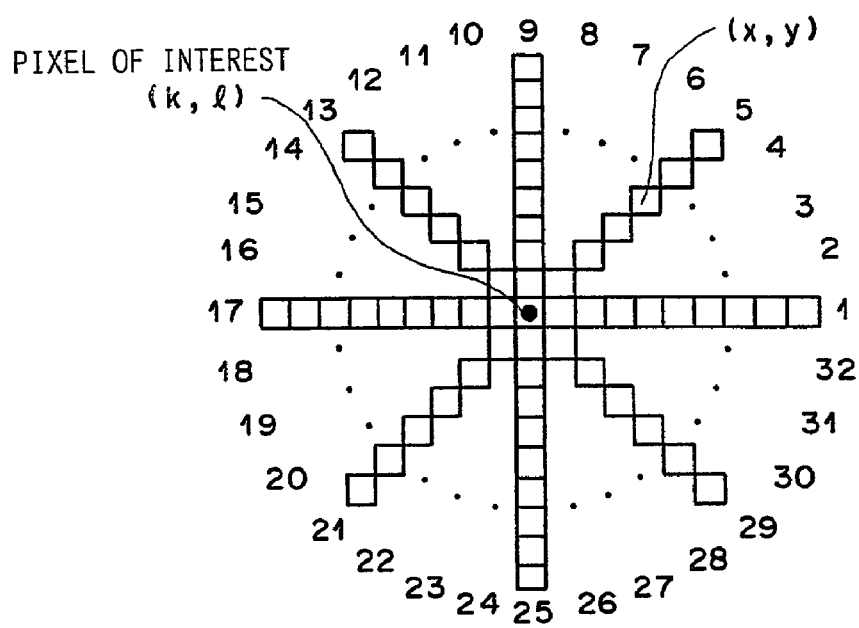
FIG. 6 is an explanatory view showing a plurality of radial lines extending radially from a pixel of interest.
Figure 7A:
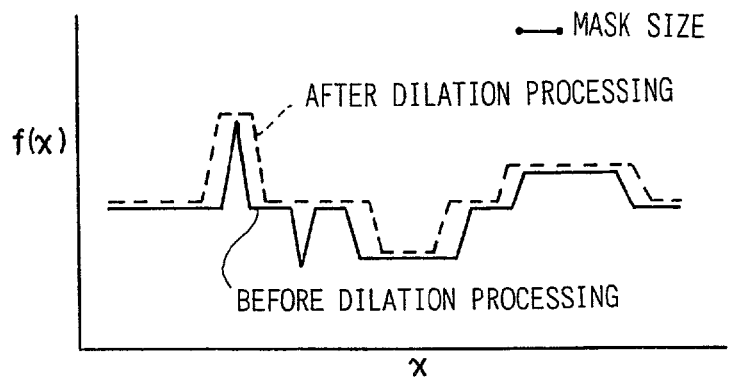
FIG. 7A is a graph showing how dilation processing, which is one of fundamental operations with a morphological filter, is performed.
Figure 7B:
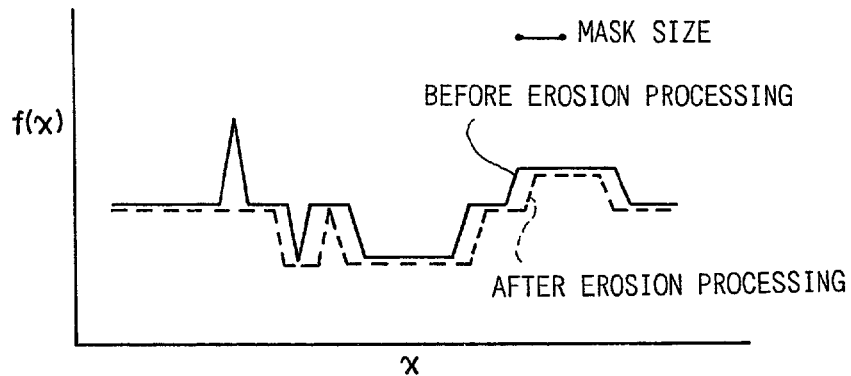
FIG. 7B is a graph showing how erosion processing, which is one of fundamental operations with a morphological filter, is performed.
Figure 7C:
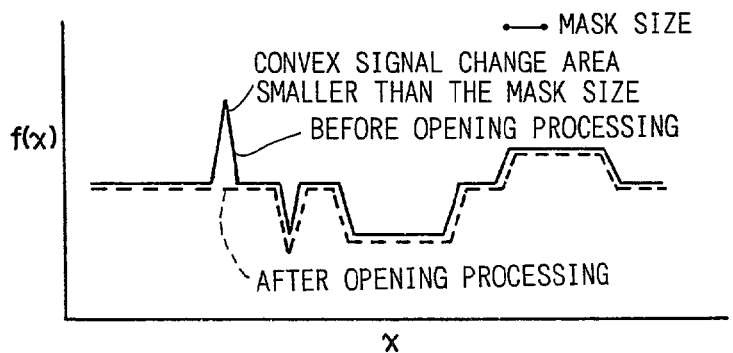
FIG. 7C is a graph showing how opening processing, which is one of fundamental operations with a morphological filter, is performed.
Figure 7D:
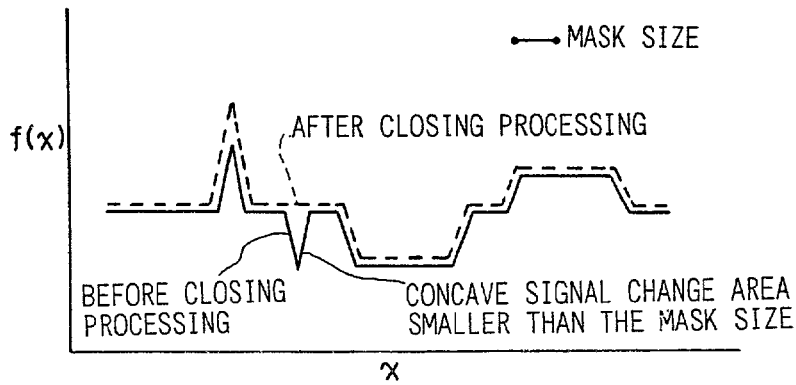
FIG. 7D is a graph showing how closing processing, which is one of fundamental operations with a morphological filter, is performed.
Figure 8:
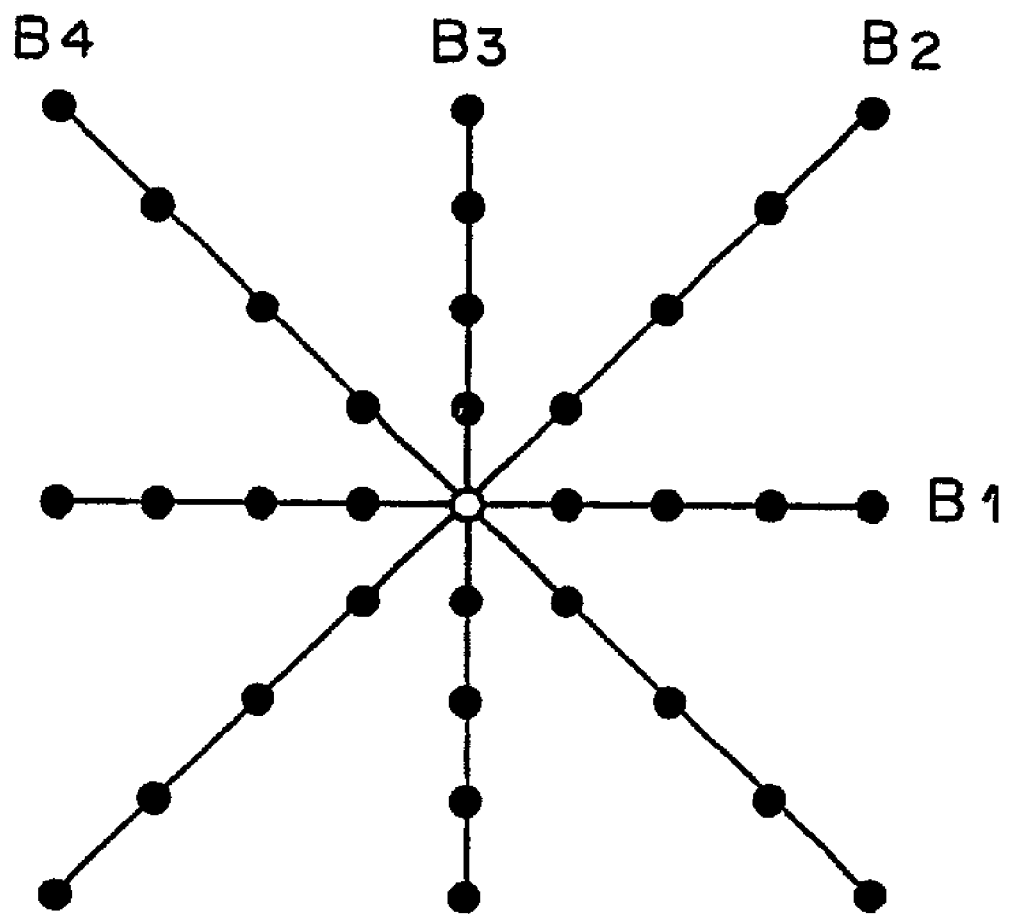
FIG. 8 is an explanatory view showing four structure elements employed in a morphological filter.
Figure 10A:
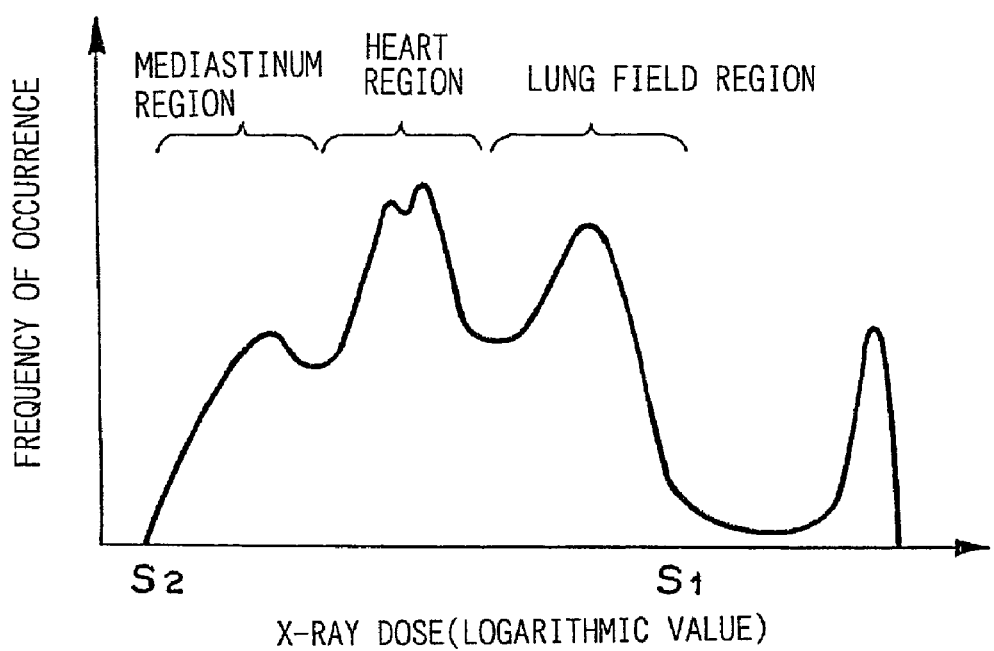
FIGS. 10A and 10B are graphs showing examples of histograms of image signals corresponding to regions inside of irradiation fields.
Figure 10B:
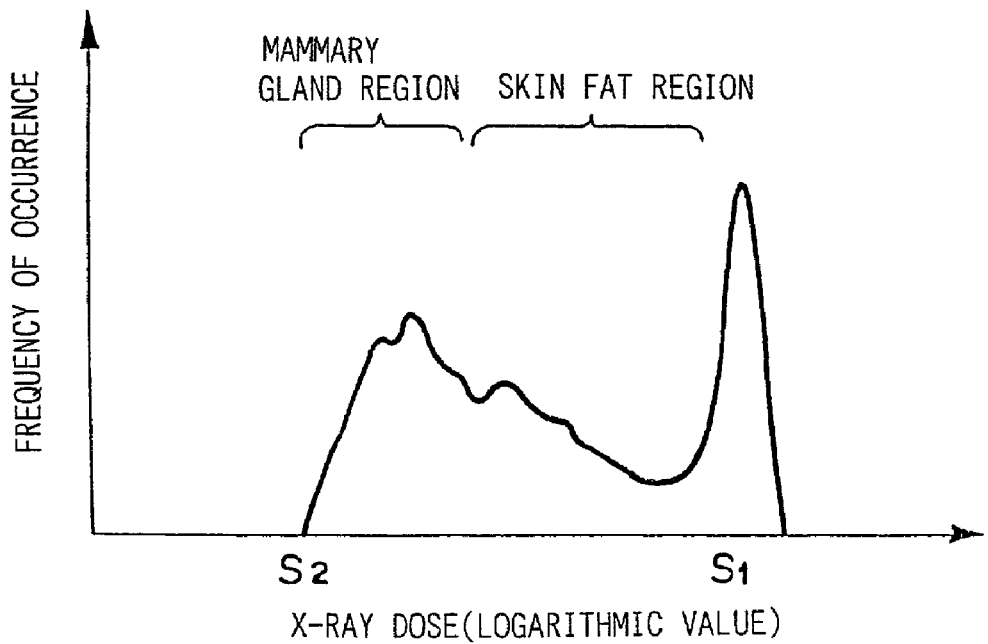
Figure 11:
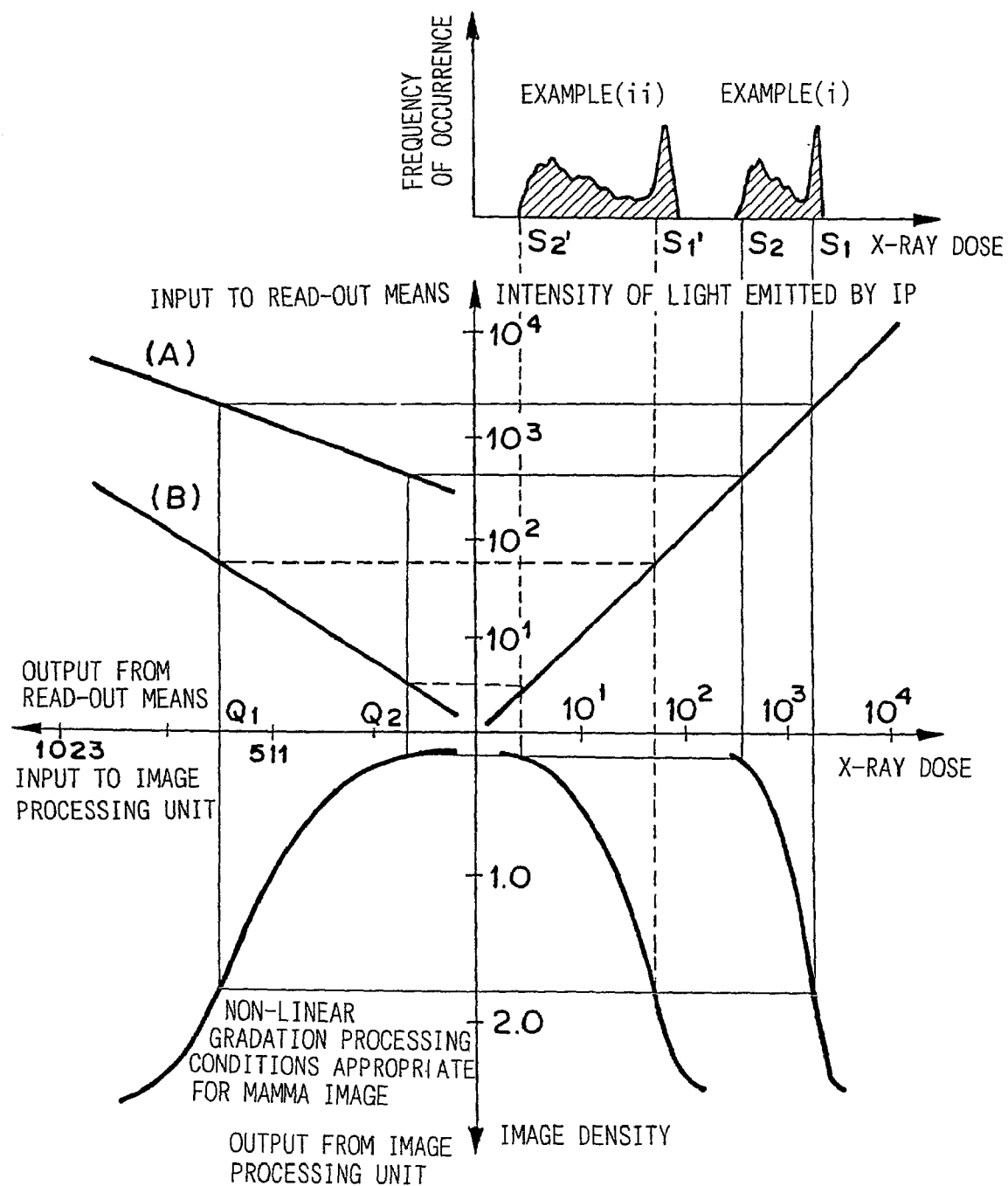
FIG. 11 is a graph showing a principle, upon which the EDR processing is based.
Figure 12:
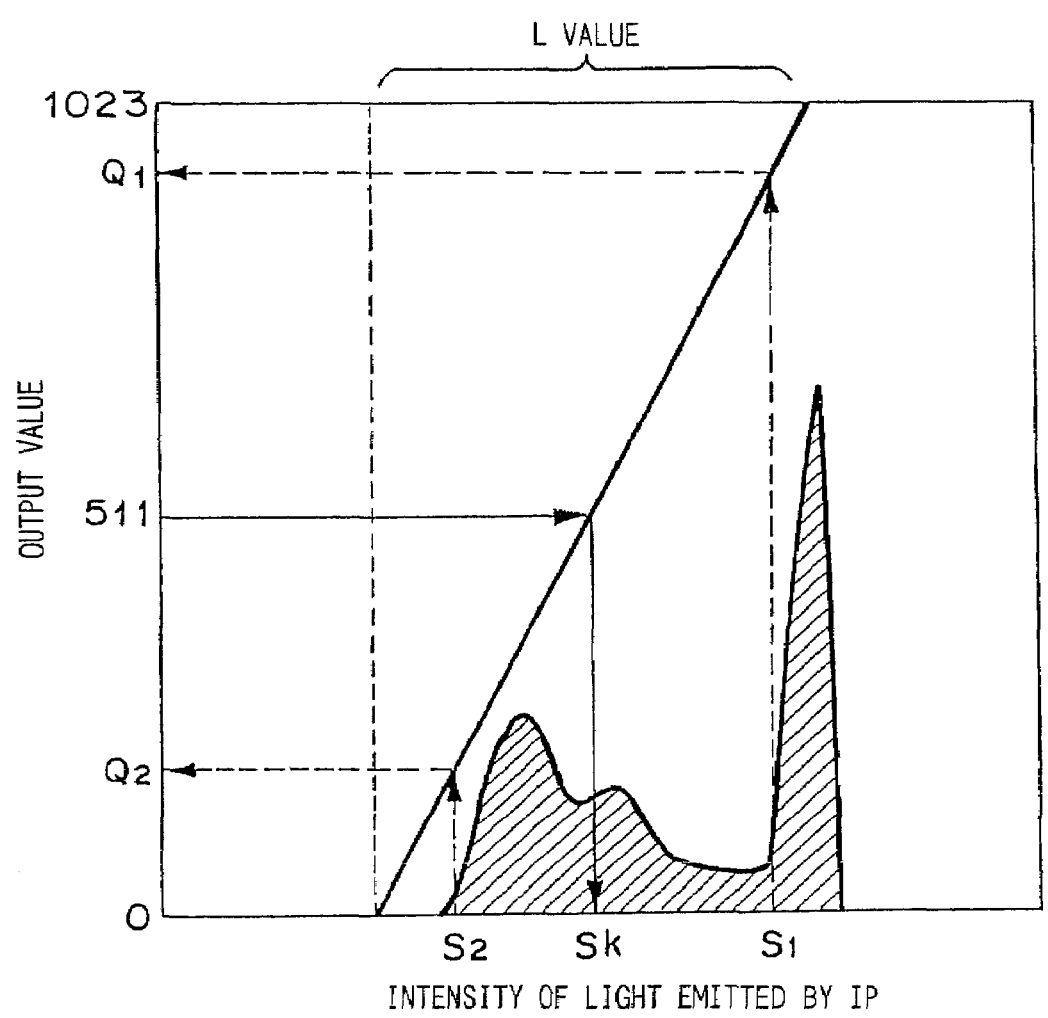
FIG. 12 is a graph showing the relationship between the intensity of light emitted by an IP and an output value, the graph serving as an aid in explaining a read-out sensitivity (S value) and a latitude (L value), which act as read-out conditions.

FIG. 3 is a graph showing numbers of abnormal pattern candidates, which have been detected in hospitals A, B, C, D, E, and F under different imaging environments. In the hospitals A, B, C, D, E, and F, the abnormal pattern candidates were detected from images obtained by performing image recording operations on the same object (the images having been subjected to the EDR processing varying for different imaging environments). From the results shown in FIG. 3, it has been found that the level of detection of the abnormal pattern candidate fluctuates in accordance with the imaging environment.

In the embodiment of the method of detecting an abnormal pattern candidate in accordance with the present invention, the image signal Qout, which is to be subjected to the abnormal pattern candidate detecting processing, is subjected to correction processing, which may be represented by Formula (2) shown below. In this manner, the fluctuation in level of detection of the abnormal pattern candidate, depending upon the imaging environment, is capable of being eliminated.

Specifically, the image signal, which has been obtained by performing the EDR processing on the image signal Qin having been obtained under a different imaging environment such that a difference in imaging environment (latitude $\Delta q$) is eliminated, maybe represented by Qout. Also, the latitude of an image signal, which has been obtained under an imaging environment acting as a reference imaging environment, may be represented by L0 (e.g., L0=2.0). In such cases, the image signal Qout is subjected to the correction processing represented by Formula (2) shown below. In this manner, the image signal Qout is converted into an image signal obtained under the imaging environment acting as the reference imaging environment.

$$Qout'=(L/L0)(Qout-Qm)+Qm \quad (2)$$

More specifically, an image signal Qout', which is obtained by performing the EDR processing by setting the L value in Formula (1) shown above at L0, may be represented by Formula (1') shown below.

$$Qout'=(RQ/Rq)(Qin-qm)/L0+Qm \quad (1')$$

In accordance with Formulas (1) and (1') shown above, it is possible to obtain Formula (2) shown above for correcting the image signal Qout, which has been obtained by performing the EDR processing with the L value=L, into the image signal Qout' such that the L value=L0.

The image signal Qout', which has been obtained by performing the correction processing in the manner described above, is one which has been converted into the image signal obtained under the reference imaging environment (latitude L0=2.0). Therefore, in cases where the noise component is removed with Formula (17) shown above, the level of the detected abnormal pattern candidate does not fluctuate for each of imaging environments.

As described above, with the embodiment of the method of detecting an abnormal pattern candidate in accordance with the present invention, the abnormal pattern candidate detecting processing performed on the image signal does not depend upon the EDR processing varying for different imaging environments. Therefore, it is not necessary to adjust the threshold value, which is utilized in the abnormal pattern candidate detecting processing, so as to conform to the imaging environment. Also, the level of erroneous detection of quantum noise and the level of detection of the abnormal pattern candidate are capable of being kept approximately at predetermined levels. Accordingly, the level of detection of the abnormal pattern candidate is capable of being kept at a predetermined level.

In the EDR processing described above, the values of qmin and qmax are detected from the histogram and are caused to correspond to Qmin and Qmax. Alternatively, an EDR processing technique may be employed, wherein a mean value qave of signal values corresponding to a specific region of the image signal Qin before being subjected to the EDR processing is employed.

Specifically, the mean value of the image signal values before being subject to the EDR processing, which image signal values correspond to a region (a region of interest) that is required to have good image quality with the EDR processing, may be represented by qave. Also, the value, which qave takes after the EDR processing has been performed, (i.e., the image signal value after the EDR processing has been performed to yield good image quality, upon which image signal value the determination of the qave value is based) may be represented by Qave. In such cases, the EDR transform maybe represented by Formula (0;b) shown below.

$$Q=(Qave/qave)\times(Qin-qm)+Qm \quad (0;b)$$

Also, instead of the L value being calculated from the signal width, the L value may be set as a representative value (a fixed value) Lfix. The representative value Lfix may be represented by the formula shown below.

$$Lfix=(qave/Rq)/(Qave/RQ)$$

In such cases, Formula (0;b) shown above maybe expressed as Formula (1;b) shown below.

$$Q=(RQ/Rq)\times(Qin-qave)/Lfix+Qave \qquad (1;b)$$

Formula (1;b) corresponds to Formula (1) shown above, wherein qm is replaced by qave, Qm is replaced by Qave, and L is replaced by Lfix. Formula (1;b) represents the processing equivalent to the processing with Formula (1). Therefore, as for the correction processing, Formula (2) shown above may be utilized.

Further, with respect to L in Formula (1) shown above, an upper limit value Lmax and a lower limit value Lmin may be determined previously. In cases where L is at least equal to Lmax, L may be set such that L=Lmax. Also, in cases where L is at most equal to Lmin, L may be set such that L=Lmin. Specifically, for example, Lmax and Lmin may be determined such that Lmax=2.5 and Lmin=1.5. In cases where $L=(\Delta q/Rq)/(\Delta Q/RQ)\geq 2.5$, L may be set such that L=2.5. In cases where $L=(\Delta q/Rq)/(\Delta Q/RQ)\leq 1.5$, L may be set such that L=1.5. In such cases, even if L takes a particularly abnormal value, the correction is capable of being made appropriately.

The threshold values T1 and T2 in Formula (17) are not altered. However, in cases where a difference between individual patients acting as the objects, such as a difference in degree of absorption of quantum noise, occurs, the difference between individual patients may be considered as being a factor of the imaging environment. Therefore, in the embodiment of the method of detecting an abnormal pattern candidate in accordance with the present invention, the threshold values T1 and T2 may be altered. In such cases, the threshold values T1 and T2 may be altered respectively with Formulas (22) and (23) shown below by utilizing the latitude $\Delta q$ with the EDR processing.

$$T1=C_1/\Delta q (C_1 \text{ is a fixed number}) \qquad (22)$$

$$T2=C_2/\Delta q (C_2 \text{ is a fixed number}) \qquad (23)$$

More specifically, as described above, in cases where the latitude $\Delta q$ with the EDR processing is large, the width of the gathered image signal values becomes small, and therefore the contrast of the area P5' of the noise component is also reduced. Accordingly, even if the threshold values are set as being small values, the microcalcification pattern P3 and the area P5' of the noise component, which is a non-calcification pattern, are capable of being discriminated from each other. In this manner, only the microcalcification pattern P3 is capable of being detected accurately.

In cases where the latitude $\Delta q$ with the EDR processing is small, the width of the gathered image signal values becomes large, and therefore the contrast of the area P5' of the noise component is also increased. In such cases, if the threshold values are fixed as in the conventional techniques, the microcalcification pattern P3 and the area P5' of the noise component, which is a non-calcification pattern, cannot be discriminated from each other. However, with this embodiment of the method for detecting an abnormal pattern candidate in accordance with the present invention, wherein the threshold values are set to be large when the L value becomes small, the microcalcification pattern P3 and the area P5' of the noise component, which is a non-calcification pattern, are capable of being discriminated from each other.

Alternatively, the threshold values T1 and T2 may be corrected respectively with Formulas (24) and (25) shown below by using the S value with the EDR processing, such that they may be in proportion to the square root of the S value. As another alternative, the threshold values T1 and T2 maybe set respectively with Formulas (26) and (27) such that they may be in inverse proportion to the latitude $\Delta q$ and in proportion to the square root of the S value.

$$T1=C_3S^{1/2}(C_3 \text{ is a fixed number}) \qquad (24)$$

$$T2=C_4S^{1/2}(C_4 \text{ is a fixed number}) \qquad (25)$$

$$T1=C_5S^{1/2}/\Delta q (C_5 \text{ is a fixed number}) \qquad (26)$$

$$T2=C_6S^{1/2}/\Delta q (C_6 \text{ is a fixed number}) \qquad (27)$$

In the aforesaid embodiment of the method of detecting an abnormal pattern candidate in accordance with the present invention, the correction processing with Formula (2) shown above is performed on the image signal, which is to be subjected to the abnormal pattern candidate detecting processing. In this manner, the abnormal pattern candidate detecting processing performed on the image signal is prevented from depending upon the EDR processing, which varies for different imaging environments. Also, the level of erroneous detection of quantum noise and the level of detection of the abnormal pattern candidate are capable of being always kept approximately at predetermined levels. Alternatively, in lieu of the image signal being subjected to the correction processing, the threshold values T1 and T2 in Formula (17) shown above may be corrected in accordance with the index value (the latitude L0), which represents the reference imaging environment. With the alternative, the same effects as those with the embodiment described above are capable of being obtained. Specifically, the threshold values T1 and T2 in Formula (17) shown above may be corrected respectively with Formulas (28) and (29) shown below.

$$T1=C_1/L0(C_1 \text{ is a fixed number}) \qquad (28)$$

$$T2=C_2/L0(C_2 \text{ is a fixed number}) \qquad (29)$$

The embodiment, wherein the abnormal pattern candidate detecting processing is performed with Formula (17), in which the thus corrected threshold values T1 and T2 are employed, constitutes an embodiment of the second method of detecting an abnormal pattern candidate in accordance with the present invention.

In the embodiment of the second method of detecting an abnormal pattern candidate in accordance with the present invention, the threshold values T1 and T2 may be corrected respectively with Formulas (30) and (31) such that they may be in inverse proportion to the latitude L0 with the EDR processing and in proportion to the square root of the S value.

$$T1=C_5S^{1/2}/L0(C_5 \text{ is a fixed number}) \qquad (30)$$

$$T2=C_6S^{1/2}/L0(C_6 \text{ is a fixed number}) \qquad (31)$$

In the aforesaid embodiments of the methods of detecting an abnormal pattern candidate in accordance with the present invention, it is assumed that the microcalcification pattern candidate is to be detected as the abnormal pattern candidate, and the relationship between the image signal and the threshold value in the morphological operation processing is corrected. However, the methods of detecting an abnormal pattern candidate in accordance with the present invention are not limited to the embodiments described above. Specifically, in the methods of detecting an abnormal pattern candidate in accordance with the present invention, the relationship between the image signal and the threshold value in the iris filter processing for detecting a tumor pattern candidate as the abnormal pattern candidate may be corrected. In such cases, in an embodiment of the second method of detecting an abnormal pattern candidate in accordance with the present invention, the threshold value T, which is to be compared with the output value C of the iris filter processing represented by Formula (7) shown above, may be corrected into T/L0 in accordance with the index value (e.g., the latitude L0) representing the reference imaging environment. Also, the threshold value processing, wherein the thus corrected threshold value T/L0 is compared with the output value C of the iris filter processing, may be performed.

What is claimed is:

1. A method of detecting an abnormal pattern candidate, in which processing for detecting an abnormal pattern candidate embedded in a medical image having been obtained from an image recording operation is performed on an image signal representing the medical image, the method comprising the steps of:
   i) in cases where the image signal is an image signal which has been subjected to predetermined signal processing, performing correction processing on the image signal such that the abnormal pattern candidate detecting processing performed on the image signal, which has been subjected to the predetermined signal processing, does not depend upon the predetermined signal processing, the correction processing is performed such that a level of detection of an abnormal pattern candidate is kept at a predetermined level, and
   ii) performing the abnormal pattern candidate detecting processing on the image signal, which has been obtained from the correction processing.

2. A method as defined in claim 1 wherein the predetermined signal processing is signal processing performed in accordance with an index value, which represents an imaging environment of the medical image.

3. A method as defined in claim 2 wherein a threshold value, which is utilized in the abnormal pattern candidate detecting processing in making a judgment as to whether a pattern is or is not the abnormal pattern candidate, is corrected in accordance with the index value, which represents the imaging environment of the medical image.

4. A method as defined in claim 1, 2, or 3 wherein the abnormal pattern candidate detecting processing is a processing, in which iris filter processing is performed on the image signal, and a tumor pattern candidate is thereby detected as the abnormal pattern candidate.

5. A method as defined in claim 1, 2, or 3 wherein the abnormal pattern candidate detecting processing is a processing, in which morphological operation processing is performed on the image signal, and a microcalcification pattern candidate is thereby detected as the abnormal pattern candidate.

6. The method of detecting an abnormal pattern candidate as defined in claim 1, wherein the predetermined image processing is a normalization process.

7. The method of detecting an abnormal pattern candidate as defined in claim 6, wherein the normalization process is exposure data recognizer (EDR) processing.

8. The method of detecting an abnormal pattern candidate as defined in claim 7, wherein a mean value of image signal values corresponding to a specific region of the image signal are used in the EDR processing.

9. A method of detecting an abnormal pattern candidate, in which processing for detecting an abnormal pattern candidate embedded in a medical image having been obtained from an image recording operation is performed on an image signal representing the medical image, the method comprising the steps of:
   i) in cases where the image signal is an image signal which has been subjected to predetermined signal processing, performing correction processing on the image signal such that the abnormal pattern candidate detecting processing performed on the image signal, which has been subjected to the predetermined signal processing, does not depend upon the predetermined signal processing, and
   ii) performing the abnormal pattern candidate detecting processing on the image signal, which has been obtained from the correction processing,
   wherein the predetermined signal processing is signal processing performed in accordance with an index value, which represents an imaging environment of the medical image, and
   wherein the signal processing is normalization processing, which may be represented by Formula (1), and the correction processing is a processing, which may be represented by Formula (2):

$$Q\text{out} = (RQ/Rq)(Q\text{in} - qm)/L + Qm \qquad (1)$$

$$Q\text{out}' = (L/L0)(Q\text{out} - Qm) + Qm \qquad (2)$$

wherein

Qin represents the image signal before being subjected to the signal processing, Qout represents the image signal after being subjected to the signal processing, qm represents the predetermined signal value before being subjected to the signal processing, Qm represents the value which qm takes after the signal processing has been performed, $L = (\Delta q/Rq)/(\Delta Q/RQ)$, Δq represents the width (latitude) of the image signal before being subjected to the signal processing, ΔQ represents the width (predetermined value) of the image signal after being subjected to the signal processing, Rq represents the signal range of Qin, RQ represents the signal range of Qout, L0 represents the reference L value, and Qout' represents the image signal after being subjected to the correction processing.

10. A method as defined in claim 9 wherein a lower limit value of L is determined previously, and the value of L is set at the lower limit value of L in cases where the value of L in Formula (2) is at most equal to the lower limit value having been determined.

11. A method as defined in claim 10, wherein an upper limit value of L is determined previously, and the value of L is set at the upper limit value of L in cases where the value of L in Formula (2) is at least equal to the upper limit value having been determined.

12. A method as defined in claim 9, wherein an upper limit value of L is determined previously, and the value of L is set at the upper limit value of L in cases where the value of L in Formula (2) is at least equal to the upper limit value having been determined.

13. A method of detecting an abnormal pattern candidate, in which processing for detecting an abnormal pattern candidate embedded in a medical image having been obtained from an image recording operation is performed on an image signal representing the medical image, the method comprising the steps of:
- i) in cases where the image signal is an image signal which has been subjected to predetermined signal processing, performing correction processing on the image signal such that the abnormal pattern candidate detecting processing performed on the image signal, which has been subjected to the predetermined signal processing, does not depend upon the predetermined signal processing, and
- ii) performing the abnormal pattern candidate detecting processing on the image signal, which has been obtained from the correction processing, wherein the predetermined signal processing is signal processing performed in accordance with an index value, which represents an imaging environment of the medical image, wherein a threshold value, which is utilized in the abnormal pattern candidate detecting processing in making a judgment as to whether a pattern is or is not the abnormal pattern candidate, is corrected in accordance with the index value, which represents the imaging environment of the medical image, and wherein the signal processing is normalization processing, which may be represented by Formula (1), and the correction processing is a processing, which may be represented by Formula (2):

$$Q\text{out}=(RQ/Rq)(Q\text{in}-qm)/L+Qm \quad (1)$$

$$Q\text{out}'=(L/L0)(Q\text{out}-Qm)+Qm \quad (2)$$

wherein

Qin represents the image signal before being subjected to the signal processing, Qout represents the image signal after being subjected to the signal processing, qm represents the predetermined signal value before being subjected to the signal processing, Qm represents the value which qm takes after the signal processing has been performed, $L=(\Delta q/Rq)/(\Delta Q/RQ)$, $\Delta q$ represents the width (latitude) of the image signal before being subjected to the signal processing, $\Delta Q$ represents the width (predetermined value) of the image signal after being subjected to the signal processing, Rq represents the signal range of Qin, RQ represents the signal range of Qout, L0 represents the reference L value, and Qout' represents the image signal after being subjected to the correction processing.

14. A method as defined in claim 13 wherein a lower limit value of L is determined previously, and the value of L is set at the lower limit value of L in cases where the value of L in Formula (2) is at most equal to the lower limit value having been determined.

15. A method as defined in claim 14, wherein an upper limit value of L is determined previously, and the value of L is set at the upper limit value of L in cases where the value of L in Formula (2) is at least equal to the upper limit value having been determined.

16. A method as defined in claim 13, wherein an upper limit value of L is determined previously, and the value of L is set at the upper limit value of L in cases where the value of L in Formula (2) is at least equal to the upper limit value having been determined.

* * * * *